US012716064B2

(12) United States Patent
Ruzsics et al.

(10) Patent No.: US 12,716,064 B2
(45) Date of Patent: Aug. 25, 2026

(54) RESCUE OF RECOMBINANT ADENOVIRUSES BY CRISPR/CAS-MEDIATED IN VIVO TERMINAL RESOLUTION

(71) Applicant: Albert-Ludwigs-Universitat Freiburg, Freiburg (DE)

(72) Inventors: Zsolt Ruzsics, DieBen am Ammersee (DE); Andre Riedl, Schweitenkirchen (DE); Julian Fischer, Freiburg (DE); Hans-Gerhard Burgert, Bad Krozingen (DE)

(73) Assignee: ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 619 days.

(21) Appl. No.: 18/028,601

(22) PCT Filed: Sep. 29, 2021

(86) PCT No.: PCT/EP2021/076757
§ 371 (c)(1),
(2) Date: Mar. 27, 2023

(87) PCT Pub. No.: WO2022/069523
PCT Pub. Date: Apr. 7, 2022

(65) Prior Publication Data

US 2025/0270545 A1 Aug. 28, 2025

(30) Foreign Application Priority Data

Sep. 29, 2020 (EP) .................................... 20198944

(51) Int. Cl.

| | |
|---|---|
| ***C12N 15/11*** | (2006.01) |
| ***C12N 7/00*** | (2006.01) |
| ***C12N 9/22*** | (2006.01) |
| ***C12N 15/86*** | (2006.01) |

(52) U.S. Cl.
CPC .............. *C12N 15/111* (2013.01); *C12N 7/00* (2013.01); *C12N 9/226* (2025.05); *C12N 15/86* (2013.01); *C12N 2310/20* (2017.05); *C12N 2710/10343* (2013.01); *C12N 2710/10352* (2013.01)

(58) Field of Classification Search
None
See application file for complete search history.

(56) References Cited

U.S. PATENT DOCUMENTS

2018/0064242 A1* 3/2018 Kotin et al. ........... C12N 15/09

OTHER PUBLICATIONS

Barretto et al., "Small circular NDAs in human pathology" Malays J Med Sci (Year: 2014).*
Yun et al., "Bacterial artificial chromosomes: a functional gemicoms tool for the study of positive-strand RNA viruses" J Vis Exp. (Year: 2015).*
Wang et al. "CRISPR/Cas9 nuclease cleavage combined with Gibsion assembly for seamless cloning" Biotechniques (Year: 2015).*
Bacterial Artificial Chromosome: edited by academic editor Pradeep Chatterjee (Year: 2011).*
Hazen "Plasmids 101: optimizing plasmid yields" Addgene (Year: 2016).*
Morris et al., "Simian adenovirus as vaccine vector" Future Viol. (Year: 2016).*
Schulz et al., "CRISPR/Cas9 delivery with one single adneoviral vector devoid of all viral genes" Sci Rep. (Year: 2017).*
Thermofisher Scientific: viral nucleic acid kits (Year: 2018).*

* cited by examiner

*Primary Examiner* — Tracy Vivlemore
*Assistant Examiner* — John David Moore
(74) *Attorney, Agent, or Firm* — Gavrilovich, Dodd & Lindsey LLP

(57) ABSTRACT

The invention relates to circular DNA molecule for rescuing recombinant adenoviruses comprising a recombinant adenoviral genome with two inverted terminal repeats (ITRs) flanking the genome ends, wherein at least one of the ITRs is associated with a target sequence adjacent to a PAM sequence, wherein the target sequence is configured for generating an RNA-guided DNA endonuclease-mediated DNA double strand break at the external end of or in close proximity outside the external end of the respective ITR, preferably within less than about 15 nucleotides. The invention also relates to a kit and a method for rescuing recombinant adenoviruses comprising or using a circular DNA molecule as described herein.

17 Claims, 8 Drawing Sheets

Specification includes a Sequence Listing.

RESCUE OF RECOMBINANT ADENOVIRUSES BY CRISPR/CAS-MEDIATED IN VIVO TERMINAL RESOLUTION

CROSS REFERENCE TO RELATED APPLICATIONS

This application is a U.S. National Phase application filed under 35 U.S.C. § 371 and claims the benefit of International Application No. PCT/EP2021/076757, filed Sep. 29, 2021, which application claim priority to European Application No: 20198944.9, filed Sep. 29, 2020, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy created on Oct. 4, 2023, named "SequenceListing_ST25.txt" and is 876,026 bytes in size.

DESCRIPTION

The invention relates to circular DNA molecule for rescuing recombinant adenoviruses comprising a recombinant adenoviral genome with two inverted terminal repeats (ITRs) flanking the genome ends, wherein at least one of the ITRs is associated with a target sequence adjacent to a PAM sequence, wherein the target sequence is configured for generating an RNA-guided DNA endonuclease-mediated DNA double strand break at the external end of or in close proximity outside the external end of the respective ITR, preferably within less than about 15 nucleotides.

The invention also relates to a kit and a method for rescuing recombinant adenoviruses comprising or using a circular DNA molecule as described herein.

BACKGROUND OF THE INVENTION

Adenoviruses are linear double stranded DNA viruses, which replicate efficiently in cell culture and recombinant adenovirus (rAd) vectors represent one of the most frequently used vehicles for gene transfer applications in vitro and in vivo. rAd genomes have been constructed in *E. coli* where their genomes can be maintained, propagated and modified in a form of circular plasmid[1] or bacterial artificial chromosome (BACs)[2,3]. The rescue of replicating rAds from their circular form derived from *E. coli* is problematic since adenovirus replication avoids circular intermediates and their linear genome is covalently linked to a terminal protein (TP)[4]. The adenovirus (Ad) genome is replicated via terminal replication origins provided by inverted terminal repeats (ITRs)—flanking the genome ends—and TP. Therefore, usually rAd-plasmids and BACs require linearization mediated by restriction endonucleases and re-purification prior to vector rescue by transfection[5]. This is in sharp contrast to rescue methodology for vectors based on other DNA viruses, such as adeno-associated virus (AAV) vectors, which replicate via circular intermediates and, therefore, their replication cycle includes naturally the switch between circular and linear genome forms (terminal resolution). In this type of vectors the rescue efficiency is dependent directly on the transfection efficiency, as disclosed in WO2019/113310A1.

WO2019/113310A1 describes the advantages of using closed-end DNA for rescue of AAV. However, AAVs are parvoviruses and their biology is very dissimilar to adenoviruses. In contrast to parvoviruses, adenoviruses do not have terminal resolution in their replication cycle. Therefore, AAV rescue experiments cannot be compared to adenovirus rescue experiments, since the AAV rescue is only dependent on the transfection efficiency, and it does not require an artificial terminal resolution step (linearization). For adenovirus-based vectors, increasing the transfection efficiency alone is not sufficient, since in addition to this the terminal resolution needs to be induced artificially.

Linear DNA transfection itself is less efficient than transfection of covalently closed circular DNA[6,7]. Moreover, another bottleneck needs to be overcome in order to reconstitute an adenovirus from linear DNA. Before DNA replication can be initiated, the genome ends require de novo TP conjugation, which is not part of the natural adenovirus DNA replication cycle[8,9].

Apart from the approach using restriction endonuclease linearization, circular DNA can only be rescued for production of rAds if the ITRs are brought in close proximity of each other[10]. The major two draw-backs of this technology are that i) the vicinity of inverted repeats can be instable in the bacteria and ii) it does not allow the removal of the bacterial vector sequences from the rAd genome upon virus rescue. Therefore, the remaining plasmid sequences either occupy about half of the cloning capacity of this vector system or additional efforts need to be undertaken to remove these sequences[10]. In addition, the ITR fusion has only been applied for rescuing species C based rAds and there are no data available whether vectors based on other Ad species can be rescued in this way. The efficiency of virus rescue via enzymatic linearization and the ITR fusion is comparable[10], but the enzymatic linearization allows direct removal of most bacterial vector sequences and applicable to wide variety of Ad species. Thus, today only the enzymatic in vitro linearization is in use for reconstitution of rAds. However, one important drawback of such restriction nuclease based applications is that they always leave extra nucleotides masking the ends of the ITRs. By lacking a methodology cutting exactly at the ends of the ITRs it was not possible to test whether the exact cleavage is an important factor in rescue efficiency.

US2002/136708A1 describes a method for production of helper-dependent adenovirus (HD-AdV) vectors. It is shown that viral DNA can be cleaved in vivo, and this cleavage efficiently inhibits the propagation of the targeted genomes. This is in contrast to the aim of the invention which is to facilitate virus propagation.

In light of the prior art there remains a significant need in the art to provide additional means for efficiently rescuing recombinant adenoviruses from transfected circular DNA, which also provides flexibility of the cleavage sites. The method known in the art using circular DNA is associated with the disadvantages of instability of the circular DNA molecule in bacteria and lack of removal of bacterial vector sequences from the rAd genome upon virus rescue, while methods employing linearized DNA have the major disadvantage of inefficient DNA transfection into the adenoviral producer cell line.

SUMMARY OF THE INVENTION

In light of the prior art the technical problem underlying the present invention is to provide alternative and/or improved means for efficiently rescuing recombinant adenoviruses from a producer cell line, wherein the rescued rAd does not comprise any bacterial vector sequences.

This problem is solved by the features of the independent claims. Preferred embodiments of the present invention are provided by the dependent claims.

The invention therefore relates to a circular DNA molecule for rescuing recombinant adenoviruses comprising a recombinant adenoviral genome with two inverted terminal repeats (ITRs) flanking the genome ends, wherein at least one of the ITRs is associated with a target sequence adjacent to a PAM sequence, wherein the target sequence is configured for generating an RNA-guided DNA endonuclease-mediated DNA double strand break at the external end of or in close proximity outside the external end of the respective ITR.

The present invention is based on the entirely surprising idea of using the CRISPR/Cas-machinery to cleave the circular DNA molecule for rescuing recombinant adenoviruses comprising a recombinant adenoviral genome rAd genomes directly in the host cells after transfection of the molecule in its circular form.

The CRISPR/Cas-technology (reviewed in Hille et al.[11]) is a precise genome editing technique with neat regulation possibilities[11] and has been applied extensively in reverse genetics of mammalian cell[12,13], viruses[14,15], and in biotefchnology[16,17]. The CRISPR/Cas9-complex introduces double strand breaks into dsDNA substrates, if there is a motif, the so-called PAM sequence or just "PAM" (ProtospacerAdjacent Motif) upstream of it. Cas9 is a multi-domain protein consisting of a recognition domain (REC), wedge domain (WED), two nuclease domains (HNH-nuclease and RuvC-like domain, respectively) and a PAM-interacting (PI) domain[18-20]. The Cas9 protein alone does not show nuclease activity, since the RuvC-like domain is blocking the HNH-nuclease domain in an auto-inhibitory fashion[21]. The transition to an endonuclease-competent state occurs, if Cas9 is associated with the sgRNA, via its REC and WED domains, detecting a target sequences via sgRNA-targeted DNA interaction. When RNA-DNA hybridization occurs, the RuvC-like domain of Cas9 is cutting the strand coding for the PAM, while its HNH-domain cuts the anti-sense strand.

Using CRISPR/Cas-technology to modify viruses is an elegant approach providing the possibility to avoid bacterial clones to propagate mutants[14,15]. However, as it is shown clearly in these papers, this method is excellent in creating mutants, but the results are i) never clonal, and ii) always contaminated with the wild type genomes. Any of these two kinds of genetic impurity may be acceptable in research (if the null phenotype dominates), but unacceptable in any kind of vector propagation technology in which clonal and pure preparations are needed. Therefore, using bacterially cloned viral genomes cannot be avoided, and the invention takes advantage of RNA-guided DNA endonucleases to turn the cloned forms to replication competent DNA. The modification of the viral genomes themselves is avoided.

CRISPR/Cas technology has been suggested for linearization of circular DNA, such as plasmid DNA, in vitro (Jia-Wang Wang et al: "*CRISPR/Cas9 nuclease cleavage combined with Gibson assembly for seamless cloning*", Biotechniques, vol. 58, no. 4, 1 Apr. 2015). However, such in vitro approaches did not appear to be attractive to assist rescue of rAds since known restriction enzyme-based in vitro linearization techniques are relatively inefficient (see above).

In the context of the present invention, the inventive circular DNA molecule, which is preferably a circular double stranded DNA molecule, comprises a target sequence adjacent to a PAM sequence. Due to the positioning of the target sequence adjacent to a PAM (adjacent meaning directly next to, without a base in between the target sequence and the PAM), the target sequence can be recognized by a suitable sgRNA associated with Cas9 or another suitable RNA-guided DNA endonuclease known to a skilled person. The skilled person is aware of the cutting site of the established RNA-guided DNA endonucleases, such as Cas9, relative to the position of the PAM sequence and the target sequence. Accordingly, it is possible to design circular DNA plasmids comprising at least one target sequence adjacent to a PAM sequence that enables generation of a DNA double strand break (namely a cut) mediated by an RNA-guided DNA endonuclease, such as Cas9, in close proximity outside the external end of the respective ITR.

By using the products and method of the present invention, it is now possible to rescue recombinant adenoviruses directly from their recombinant form without further manipulation. Thus, this method is simpler and faster than the traditional methodology for reconstitution of recombinant adenoviruses. One major technical gain with this new technology of the present invention, however, is that the virus rescue is about 30-50 fold more efficient than any other described technology for rAd rescue. This makes this technology a much better platform for application, which are determined by primary virus recue, such as preparation of high content vector libraries or propagation of plasmid based high capacity adenovirus vectors.

In preferred embodiments, the target sequence and PAM sequence are selected and designed in a way, that the cut is occurring directly outside of the external end of the ITR, meaning directly after the last base pair forming part of the ITR. In a preferred embodiment of the invention, each of the two ITRs is associated with a target sequence adjacent to a PAM sequence. To our knowledge, this invention is the first approach that allows cutting out the rAd genome from its circular form precisely at the very ends of the viral ITRs.

However, as used herein, the term "close proximity" relates to cuts generated by the RNA-guided endonuclease that are located in the range of 0-40 bases outside the external end of the ITR, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 bases outside the external end of the ITR.

In preferred embodiments, the DNA cuts generated by the RNA-guided endonuclease are located in within 25, more preferably within 20, even more preferably with 15, and even more preferably within 10 nucleotides outside the external end of the respective ITR. As is evident from the data of the examples, rescue efficiency increases with increasing proximity of the cut to the external end of the ITR, at least for some ITR sequences and corresponding target sequences.

In the most preferred embodiment, the one or preferably two DNA double strand breaks are generated exactly at the external end of the one or preferably two respective ITRs. However, the invention also functions well if the DSBs are generated in close proximity outside the external end of the respective ITR, in particular if the DSBs war within less than 20 bases outside the external end of the ITR, such as 19, 18, 17, 16, 15, 14, 13, 12, 11, 10, 9, 8, 7, 6, 5, 4, 3, 2, or 1 base outside the external end of the ITR.

In a preferred embodiment of the invention, each of the two ITRs is associated with a target sequence adjacent to a PAM sequence.

Although it was shown that presence of one target sequence adjacent to a PAM sequence configured for generating an RNA-guided DNA endonuclease-mediated DNA double strand break at the external end of or in close proximity outside the external end of the respective ITR is sufficient to enable efficient rescue of recombinant adenoviruses after intracellular processing by Cas9, it turned out that induction of two double strand breaks outside each of the two ITRs results in much higher efficiency of viral rescue form the cells. In such embodiments, each of the two ITRs of the recombinant adenoviral genome comprised by the circular DNA molecule of the invention is associated with a target sequence and adjacent PAM which are configured for enabling cutting by a RNA-guided endonuclease directly outside the ITR sequence or in close proximity, as defined herein.

In embodiments relating to circular DNA molecules of the invention in which both ITRs are associated with a target sequence adjacent to a PAM sequence, the respective target sequences associated with the two ITRs are identical or different to rescue different rAd types.

Since the ITR sequences derived from different types of adenoviruses are mostly not identical, it will often not be possible to use identical target sequences adjacent to a PAM sequence in order to generate an RNA-endonuclease mediated double strand breaks directly outside of the actual ITR, namely directly outside the last base/base-pair comprised by the ITR at its external end. Such exact cutting often requires PAM and/or target sequence to overlap the outside end of the ITR sequence and the adjacent sequence of the circular DNA molecule, depending on the cutting behavior of the employed RNA-guided endonuclease.

For example, in case of using Cas9, the double strand break will occur 3-4 bases upstream of the PAM sequence. Accordingly, in order to induce an exact cutting by Cas 9 the PAM sequence has be located either 3 bases inside or 3 bases outside the ITR while the target sequence extends upstream of the PAM either comprising the last 3 bases of the ITR and additional bases outside the ITR or comprising the first 3 bases outside ITR and additional bases inside the ITR.

Accordingly, if exact cutting outside at the ITRs is intended, it will often be necessary to use two different target sequence associated with ITRs of different types of adenoviruses, due to the different sequence of the ends of their ITRs.

Such embodiments enabling induction of double strand breaks directly outside the two ITRs can be highly advantageous for applications that require high efficiency of virus rescue.

In embodiments, the PAM and/or the target sequence are at least partially overlapping with the external end of the ITR, wherein preferably the target sequence is configured for generating an RNA-guided DNA endonuclease-mediated DNA double strand break at the external end of the respective ITR. Such embodiments are advantageous, if exact cutting just outside the ITR is required. In the context of the invention, PAM sequence and target sequence form a continuous sequence, and it is understood that if this continuous sequence is extending across the border of the ITR and the adjacent sequence of the circular DNA molecule that is not part of the recombinant adenoviral genome the continuous sequence is partially overlapping with the external end of the ITR.

However, as shown in the examples, efficient rescue of rAd is also possible if the double strand breaks outside the ITR are not occurring exactly outside the ITR but instead in close proximity to the ITRs outside of the ITRs. Therefore, it is possible to design and genetically engineer circular DNA molecules of the invention comprising suitable identical target sequences that are preferably located outside of the ITR and enable cutting within few nucleotides outside of the ITR, for example about 6-7 nucleotides outside the ITRs.

By engineering the sequence outside the ITRs it is possible to provide circular DNA molecules that comprise two identical target sequences adjacent to a PAM that are associated with the two ITRs of the DNA molecule. Accordingly, it is possible to induce two double strand breaks outside the two ITRs of the molecules by using only a single guide RNA (gRNA) that directs the RNA-guided endonuclease to both ITRs for cutting the circular DNA molecule and providing free ends of dsDNA just outside both ITRs.

It is a great advantage that it is possible to engineer circular DNA molecules of the invention with identical target sequences that are associated with the ITRs of any types of adenoviruses, since the same target sequence and consequently the same gRNA could be used to rescue rAds derived from different types of adenoviruses.

In embodiments, the target sequence or the PAM is located adjacent to the external end of the ITR. In such embodiments, the circular DNA molecule is designed in a way that the first nucleotide outside an ITR is either part of the target sequence, or preferably is the first of the three nucleotides of the PAM. For example, adjacent to the ITR there is the PAM sequence directly followed by the target sequence. In case of Cas9 mediated cutting the double strand break will be generated 6 nucleotides outside of the ITR sequence.

In other embodiments, the target and PAM sequence are arranged adjacent to the ITR in the other directing, wherein outside and adjacent to the ITR there is first the target sequence which is followed by the PAM. It is possible to engineer the circular DNA molecule of the invention in a way that outside and adjacent to both ITR sequence the same target sequence and PAM are located. In such embodiments where the PAM is directly adjacent to the ITRs followed by the target sequence, this enables generation of two double strand breaks at about 6 nucleotides outside each ITR by using only a single gRNA.

As used herein, the term "adjacent" relates to sequences or bases that are located directly next to each other without other bases being located in between. Accordingly, if for example a PAM is located adjacent to (the external end of) an ITR, this means that the first base outside the ITR that is not part of the ITR is part of the PAM.

Accordingly, in embodiments the target sequences associated with the two ITRs are identical.

In the context of the invention, a target sequence is referred to as being associated with an ITR is the target sequence together with the adjacent PAM enables the generation of an RNA-endonuclease mediated double strand break directly outside, or in close proximity to the external end of the respective ITR.

In embodiments of the invention, the circular DNA molecule is a bacterial artificial chromosome (BAC). In such embodiments, the recombinant adenoviral genome is integrated into a much larger BAC. Using such BAC based circular DNA molecules is advantageous due to the large cloning capacity of BACs which enables for example also delivery of DNA sequence enabling expression of one, two or more gRNAs and/or Cas9 or another suitable RNA-guided endonuclease within the same DNA molecule.

In another embodiment, the circular DNA molecule is a high copy plasmid. Such embodiments are highly advantageous for high efficiency applications requiring high quality of DNA and introduction multiple copies of the circular DNA molecule into the producing cells. In such embodiments employing circular high copy plasmids comprising the recombinant adenoviral genome, it can be preferred to provide the gRNA and Cas9 or another RNA-guided endonuclease encoding sequences either on different DNA molecules, such as other plasmids, or to use producing cells lines already expressing these molecules.

In embodiments, the circular DNA molecule additionally comprises an expression cassette for at least one guide-RNA (gRNA) and/or an expression cassette for an RNA-guided DNA endonuclease generating DNA double strand breaks, such as *S. pyogenes* Cas9 (SpCas9), wherein the expression cassette(s) is/are located between the two ITRs outside the adenoviral genome. For example, BAC-based circular DNA molecules of the invention have sufficient cloning capacity to also provide such expression cassettes within the same molecule, enabling production of rAd in unmodified producing cells by delivery of only a single DNA molecule.

In embodiments of the invention, the adenoviral genome is a human adenoviral vector genome.

In further embodiments, the adenoviral genome is a simian adenoviral vector genome. The use of simian adenoviral vectors is advantageous when using the recombinant adenoviral vectors for gene delivery to human subjects that may have antibodies against human adenoviruses. The simian vectors are not recognized by such existing antibodies and are therefore not recognized by the host immune system.

In embodiments, the adenoviral genome is an adenoviral vector genome, such as a first-, second- or third-generation adenoviral vector genome, preferably comprising at least one transgene.

In embodiments, the adenoviral genome is a first-generation adenoviral vector genome, preferably comprising at least one transgene. In further embodiments, the adenoviral genome is a second-generation or third-generation adenoviral vector genome, preferably comprising at least one transgene.

The present invention further relates to a kit for rescuing recombinant adenoviruses comprising a. a circular DNA molecule or the invention, and
b. an RNA-guided DNA endonuclease or a nucleic acid molecule encoding an RNA-guided DNA endonuclease,
c. one or more gRNAs or one or more nucleic acid molecules encoding one or more gRNAs for targeting an RNA-guided DNA endonuclease to the targeting sequences of the circular DNA molecule, and/or
d. cells suited for rescuing recombinant adenoviruses (producing cells), such as 293 cells or A549 cells.

It is understood that a nucleic acid molecule encoding an RNA-guided DNA endonuclease or encoding a gRNA is a nucleic acid molecule enabling expression of an RNA-guided DNA endonuclease or a gRNA, such as a nucleic acid molecule comprising a respective expression cassette, wherein such an expression cassette comprises the coding sequence operably linked to a promoter and/or enhancer sequence mediating transcription and expression of the coding sequence.

In embodiments, the kit of the invention comprises cells suited for rescuing recombinant adenoviruses, wherein the cells express an RNA-guided DNA endonuclease, preferably SpCas9.

Furthermore, the present invention also relates to an in vitro method for rescuing recombinant adenoviruses, the method comprising a. providing cells suited for rescuing recombinant adenoviruses, such as 293 cells,
b. introducing into said cell a circular DNA molecule of the invention comprising a recombinant adenoviral genome with two inverted terminal repeats (ITRs) flanking the genome ends, wherein at least one of the ITRs is associated with a target sequence adjacent to a PAM sequence, wherein each of the target sequences is configured for generating an RNA-guided DNA endonuclease-mediated DNA double strand break at the external end of or in close proximity outside the external end of the respective ITR,
c. providing inside the cell an RNA-guided DNA endonuclease and at least one gRNA for targeting the RNA-guided DNA endonuclease to the target sequence of the circular DNA molecule,
d. linearizing recombinant adenoviral genome comprising the two ITRs inside the cells,
e. collecting viral particles from the cell supernatant.

Specific embodiments of the invention are disclosed in the examples below. These include the plasmids pO6-A5-mChe-WH, the warhead-modified species C BACs pBWH-C5-mChe, pBWH-C5-mChe-Cas9, pBWH-L-C5-mChe, pBWH-R-C5-mChe, and pBWH-C5-gRNA-mChe, species D BAC pBWH-D64M-GFP, species E BACs pBWH-E04 and pBHW-SE25, species B plasmid pLWH-B03, and species C plasmid pAC05-CE1.

In specific embodiments of the invention, the plasmids pAR-gRNA-Cas9-Amp, pAR-gRNA-Ex, pAR-gRNA-IntC5, pAR-gRNA-IntD64, pSG5-Cas9, pBAd5-mChe, pBAd5-FG40-GFP and/or pBWH-C5-mChe-DD-Cas9 can be used in the context of the method of the invention or can be comprised by the kit of the invention.

The disclosed plasmids of the invention correspond to the following sequences:

| Plasmids | SEQ ID NO. |
|---|---|
| pO6-A5-mChe-WH | SEQ ID NO. 35 |
| pBWH-C5-mChe | SEQ ID NO. 36 |
| pBWH-C5-mChe-Cas9 | SEQ ID NO. 37 |
| pBWH-L-C5-mChe | SEQ ID NO. 38 |
| pBWH-R-C5-mChe | SEQ ID NO. 39 |
| pBWH-C5-gRNA-mChe | SEQ ID NO. 40 |
| pBWH-D64M-GFP | SEQ ID NO. 41 |
| pBWH-E04 | SEQ ID NO. 42 |
| pBHW-SE25 | SEQ ID NO. 43 |
| pLWH-B03 | SEQ ID NO. 44 |
| pAC05-CE1 | SEQ ID NO. 45 |
| pAR-gRNA-Cas9-Amp | SEQ ID NO. 46 |
| pAR-gRNA-Ex | SEQ ID NO. 47 |
| pAR-gRNA-IntC5 | SEQ ID NO. 48 |
| pAR-gRNA-IntD64 | SEQ ID NO. 49 |
| pSG5-Cas9 | SEQ ID NO. 50 |
| pBAd5-mChe | SEQ ID NO. 51 |
| pBAd5-FG40-GFP | SEQ ID NO. 52 |
| pBWH-C5-mChe-DD-Cas9 | SEQ ID NO. 53 |
| pAR-gRNA-Int4-Cas9-Amp | SEQ ID NO. 54 |
| pO6-A5-WH18/19-mChe | SEQ ID NO. 55 |
| pBWH18/19-C5-mChe | SEQ ID NO. 56 |
| pBWH-E4-DE3 | SEQ ID NO. 57 |

With respect to the disclosed oligonucleotides (primers), synthetic DNA fragments and further sequences used for constructing circular DNA molecules and plasmids of the invention disclosed herein, in particular DNA sequences SEQ ID NO. 1-34 and SEQ ID NO. 58-64, as well as the plasmids according to SEQ ID NO. 35-57, these are not intended to limit the scope of the invention, but represent preferred embodiments of aspects of the invention provided for greater illustration of the invention described herein. The invention also relates to DNA sequences selected from the group comprising:

- one or more sequence comprising a fragment of the respective sequences SEQ ID NO. 1-64;
- one or more nucleic acid molecules which are complementary to the respective sequences SEQ ID NO. 1-64 in accordance with a);
- one or more nucleic acid sequence which undergo hybridization with the nucleotide sequences according to a) or b) under stringent conditions;
- one or more nucleic acid sequences comprising a nucleotide sequence having sufficient sequence identity to be functionally analogous the nucleotide sequences according to a), b) or c);
- one or more nucleic acid sequences which, because of the genetic code, are degenerated into nucleotide sequences according to a) through d); and
- one or more nucleic acid sequences according the nucleotide sequences of a) through e) which are modified by deletions, additions, substitutions, translocations, inversions and/or insertions and functionally analogous to a nucleotide sequence according to a) through e).

Accordingly, the invention encompasses nucleic acid sequence with at least 60%, preferably 70%, more preferably 80%, especially preferably 90% sequence identity to the nucleic acid sequences SEQ ID NO. 1-64.

Sequence variants of the described specific nucleic acids sequence comprised by the invention, for example defined by the provided % sequence identity, that maintain the said properties of the invention are also included in the scope of the invention. Such variants, which show alternative sequences, but maintain essentially the same properties as the specific sequences provided are known as functional analogues, or as functionally analogous. Sequence identity relates to the percentage of identical nucleotides or amino acids when carrying out a sequence alignment, for example using software such as BLAST.

It is understood that all possible of preferred features of the circular DNA molecule of the invention are herewith also disclosed in the context of the kit and the method of the invention. The other way around, features that are disclosed in the context of the kit or method of the invention also relate to the circular DNA molecule of the invention.

DETAILED DESCRIPTION OF THE INVENTION

All cited documents of the patent and non-patent literature are hereby incorporated by reference in their entirety.

The present invention is directed to a circular DNA molecule for rescuing recombinant adenoviruses comprising a recombinant adenoviral genome with two inverted terminal repeats (ITRs) flanking the genome ends, wherein

- at least one of the ITRs is associated with a target sequence adjacent to a PAM sequence, wherein
- the target sequence is configured for generating an RNA-guided DNA endonuclease-mediated DNA double strand break at the external end of or in close proximity outside the external end of the respective ITR.

Adenoviruses are members of the family Adenoviridae and have a medium size of about 90-100 nm. They are nonenveloped (without an outer lipid bilayer) viruses with an icosahedral nucleocapsid containing a double stranded DNA genome. They have a broad range of vertebrate hosts; in humans, more than 50 distinct adenoviral serotypes have been found to cause a wide range of illnesses, from mild respiratory infections in young children (known as the common cold) to life-threatening multi-organ disease in people with a weakened immune system. The present invention is directed to provision of DNA molecules as well as methods and material for rescuing recombinant adenoviruses of all kind. However, human and simian adenoviruses are preferred. Furthermore, the invention also relates to rescue of adenoviral vectors, which are derived from all kinds of adenoviruses, such as human or simian adenoviruses of various serotypes.

Classification of Adenoviridae can be complex. In humans, there are about 100 accepted human adenovirus types in seven species (Human adenovirus A to G; according to the ICTV 9th Report (2011) available under: https://talk.ictvonline.org/ictv-reports/ictv_9th_report/dsdna-viruses-2011/w/dsdna_viruses/93/adenoviridae; see also Lefkowitz et al. Nucleic Acids Res. 2018 Jan. 4; 46(D1): D708-D717, doi: 10.1093/nar/gkx932). The numbering of the types (between 1-57) are identical with the earlier used numbers for the serotypes: A: 12, 18, 31; B: 3, 7, 11, 14, 16, 21, 34, 35, 50, 55; C: 1, 2, 5, 6, 57; D: 8, 9, 10, 13, 15, 17, 19, 20, 22, 23, 24, 25, 26, 27, 28, 29, 30, 32, 33, 36, 37, 38, 39, 42, 43, 44, 45, 46, 47, 48, 49, 51, 53, 54, 56; E: 4; F: 40, 41; G: 52. For isolates, which could not be classified by serology and the newly identified types a number was/is given by the ICTV committee in the order of their acceptance. The present invention comprises and is useful for all know adenovirus types, and it can be expected that it is also applicable to newly identified types of adenoviruses, which carry terminal ITR.

Different types/serotypes are associated with different conditions: respiratory disease is mainly species HAdV-B and C; conjunctivitis often occurs with HAdV-B and D; gastroenteritis is often associated with HAdV-F types 40, 41, HAdV-G type 52; obesity or adipogenesis are often induced by HAdV-A type 31, HAdV-C type 5, HAdV-D types 9, 36, 37.

The present invention is not restricted to adenoviruses infecting humans (herein referred to as human adenovirus or (if referring to the viral genome) human adenoviral genome), but also comprises adenoviruses infecting other animals, such as monkey or chimpanzees.

Comprised are in particular simian mastadenoviruses, in particular simian mastadenovirus A, B and E, are adenoviruses infecting simians. Also comprised are adenoviruses that have initially been isolated from chimpanzees, which may be are classified into "human" adenovirus species because of their great similarity to certain human adenoviruses (HAdVs). For example, the simian adenoviruses SAdV-22 to SAdV-25 belong to the species human mastadenovirus E and SAdV-21 to the species human mastadenovirus B.

When not restricting the subject to human viruses, Adenoviridae can be divided into five genera: Mastadenovirus, Aviadenovirus, Atadenovirus, Siadenovirus, and Ichtadenovirus, all of which can be subject of the present invention.

The genus Atadenovirus comprises bovine atadenovirus D in cattle, possum atadenovirus A in opossum; ovine atadenovirus D in sheep; deer atadenovirus A in deer; lizard atadenovirus A in bearded dragons, chameleon, gecko; snake atadenovirus A in snakes; psittacine atadenovirus A in parrots; duck atadenovirus A in ducks. The genus Aviadenovirus fowl aviadenovirus A-E (avian influenza viruses) in geese and poultry; goose aviadenovirus A in geese; duck aviadenovirus B in ducks; pigeon aviadenovirus A and B in pigeons; falcon aviadenovirus A in falcons; psittacine aviadenovirus B in parrots; turkey aviadenovirus B to D in turkeys. The genus Ichtadenovirus comprises sturgeon ichtadenovirus A aka white sturgeon adenovirus in white sturgeon. The genus Mastadenovirus comprises human mastadenovirus A-F (HAdV-A to HAdV-F) in humans and some also in simians, such as chimpanzees; bovine mastadenovirus A to C in cattle; canine mastadenovirus A; equine mastadenovirus A in horses; ovine mastadenovirus A and B in sheep; porcine mastadenovirus A in pigs; simian mastadenovirus A in monkeys; tree shrew mastadenovirus A in Tupaias; “Caprines Adenovirus” (Goat adenovirus 2, GAdV-2) in goats; “Guinea Pig Adenovirus in guinea pigs; “Ovines adenovirus C” (Ovine adenovirus 6, OAdV-6) in sheep. The genus Siadenovirus comprises frog siadenovirus A aka Frog siadenovirus 1 in frogs; great tit siadenovirus A in great titmice; penguin siadenovirus A in penguins; raptor siadenovirus A in birds of prey; skua siadenovirus A in skuas; turkey siadenovirus A aka turkey siadenovirus A in turkeys.

As shown in the examples, the invention is not restricted to human adenoviruses but also works for simian adenoviruses, for example, and there is no reason to believe that it would be restricted to a specific genus or species, type or serotype of adenovirus.

Adenoviruses represent the largest known nonenveloped viruses which can be transported through the endosome (i.e., envelope fusion is not necessary). The virion also has a unique “spike” or fiber associated with each penton base of the capsid that aids in attachment to the host cell via the receptor on the surface of the host cell.

The adenovirus genome comprised by the virion (viral particle) is linear, non-segmented double-stranded (ds) DNA that is usually between 26 and 48 Kbp. This allows the virus to theoretically carry 22 to 40 genes. The viral genome has a terminal 55 kDa protein associated with each of the 5' ends of the linear dsDNA. These are used as “primers” in viral replication and ensure that the ends of the virus' linear genome are adequately replicated.

As used herein, it is understood that in the context of the circular DNA molecule of the invention comprising a recombinant adenoviral genome, the DNA sequence of a recombinant adenoviral genome to be packaged into a viral particle is comprised by the circular DNA molecule. In the context of the invention, the circular DNA molecule comprising the sequence of the recombinant adenoviral genome is introduced into the producing cell. Therein it is linearized by means of an RNA-guided endonuclease, preferably using the CRISPR/Cas system, and the resulting linear DNA molecule comprising or consisting of the sequence of the recombinant adenoviral genome can be replicated and packaged into viral particles produces by the cells.

Adenoviruses possess a linear dsDNA genome which is replicated in the nucleus of vertebrate cells using the host's replication machinery. Entry into the host cell is initiated by the knob domain of the fiber protein binding to the cell receptor, such as CD46 for the group B human adenovirus serotypes and the coxsackievirus adenovirus receptor (CAR) for all other serotypes. There are some reports suggesting MHC molecules and sialic acid residues functioning in this capacity as well. This first interaction is followed by a secondary interaction, where a motif in the penton base protein (see capsomere) interacts with av integrin, functioning as a co-receptor interaction stimulating entry of the adenovirus. Binding to av integrin results in endocytosis of the virus particle via clathrin-coated pits. Attachment to av integrin stimulates cell signaling and thus induces actin polymerization resulting in entry of the virion into the host cell within an endosome.

Once the virus has entered the host cell, the endosome acidifies, which alters virus topology by causing capsid components to disband. The capsid is destabilized, and protein VI is released from the capsid. These changes, as well as the toxic nature of the pentons, destroy the endosome, resulting in the movement of the virion into the cytoplasm. With the help of cellular microtubules, the virus is transported to the nuclear pore complex, whereby the adenovirus particle disassembles. Viral DNA is then released and can enter the nucleus. After this the DNA associates with histone molecules and viral gene expression can occur and new virus particles can be generated.

The adenovirus life cycle is divided in two phases: an early and a late phase. In both phases, a primary transcript that is alternatively spliced to generate monocistronic mRNAs compatible with the host's ribosome is generated, allowing for the products to be translated. The early genes are responsible for expressing mainly non-structural, regulatory proteins. The goal of these proteins is threefold: to alter the expression of host proteins that are necessary for DNA synthesis; to activate other virus genes (such as the virus-encoded DNA polymerase); and to avoid premature death of the infected cell by the host-immune defenses (blockage of apoptosis, blockage of interferon activity, and blockage of MHC class I translocation and expression). DNA replication separates the early and late phases. Once the early genes have liberated adequate virus proteins, replication machinery, and replication substrates, replication of the adenovirus genome can occur. A terminal protein that is covalently bound to the 5' end of the adenovirus genome acts as a primer for replication. The viral DNA polymerase then uses a strand displacement mechanism, as opposed to the conventional Okazaki fragments used in mammalian DNA replication, to replicate the genome. The late phase of the adenovirus lifecycle is focused on producing sufficient quantities of structural protein to pack all the genetic material produced by DNA replication. Once the viral components have successfully been replicated, the virus is assembled into its protein shells and released from the cell as a result of virally induced cell lysis.

Adenovirus (Ad) has received tremendous attention as an effective gene delivery vector and was in fact the first DNA virus to enter rigorous therapeutic development, due to its well-defined biology, its genetic stability, its high gene transduction efficiency and its ease of large-scale production. Ad serotypes differ in tropism and are further divided into six subgroups, A-G. Differences in viral capsids delineate tropisms among serotypes. The viral capsid is comprised of capsid proteins, core proteins, and cement proteins. These diverse serotypes can give rise to a vast range of therapeutic candidate viruses.

Adenoviral vectors offer important advantages: First, adenovirus is the most effective means of delivering genes in vivo as most human cells express the primary adenovirus receptor and the secondary integrin receptors. Thus, are easily infected with adenovirus vectors and consequently yield high levels of the transgene expression. Second, the development of “gutless” adenoviral vectors allows us to circumvent anti-adenoviral vector immunity. Third, there has been extensive experience with adenovirus vectors in many different clinical applications, and the safest dosing and routes of administration are well established. Fourth, adenovirus vectors offer a versatile platform for developing strategies to modify viral capsids in order to enhance therapeutic properties and improve targeting specificity of the virus. Interestingly, some of the inherited shortcomings of adenovirus, such as immunity evoked against the adenovirus capsid and low-level expression of adenovirus genes, may now prove beneficial for the development of anticancer immunotherapies, where inducing immunity against the cancer or directly killing the cancer cell is the goal. Furthermore, the combined immunity against the adenovirus together with the short time of expression is ideal for using the adenovirus as a platform for developing vaccines. However, depending on the application, the use of the rare serotypes 2 and 5 to construct adenoviral vectors for gene therapy can be advantageous to avoid preexisting immunity.

Adenoviral vectors can transduce both replicating and quiescent cell populations, making them a valuable tool in delivering transgenes in vivo and within mature tissues. In contrast to lentiviral vectors, adenoviral vectors can deliver larger transgenes up to 8 kbp in size; however, their DNA does not integrate into the host genome, but rather, resides episomally in the host nucleus. Such episomal transduction precludes the risks of insertional mutagenesis, without direct integration into the host genome.

The adenoviral genomes are linear, non-segmented double-stranded DNA with sizes ranging from 26 kb to 45 kb in length, depending on the serotype. The genome of the commonly used human adenovirus type 5 (HAdV-5) is approximately 36 kb. The genomic DNA or genomic sequence is flanked on both ends by hair-pin-like, inverted terminal repeats (ITR), which serve a variety of purposes. One of the roles of ITRs is to act as a self-primer to promote primase-independent DNA synthesis, making them important elements in DNA multiplication. Another function of the ITRs is to facilitate integration into the host genome. In addition to ITRs, another genetic element of the adenovirus is the packaging signal, which is located on the left arm of the genome and is required for proper viral transcript packaging. Viral transcripts are classified as either early or late. The four early transcriptional units, E1, E2, E3, and E4, are responsible for expressing non-structural proteins having regulatory functions in particular in viral DNA replication. The late proteins encode for structural components of the Ad virion.

To establish safety in use of adenoviral vectors, essential viral-replication genes were eliminated. First generation adenoviral vectors are those stripped of regulatory genes E1a and E1b—the first transcriptional regulatory factors to be produced during the viral life cycle. The depletion of this gene resulted in replication-deficient adenoviral vectors with an initial transgene cloning capacity of 5.2 kb.

To increase cloning capacity and continue to decrease capacity for viral replication, second generation adenoviral vectors were developed by deletion of other non-structural genes (E2/E3/E4) in addition to the original E1 gene absent in first generation vectors. While the second generation of vectors demonstrated increased cloning capacity and reduced cytotoxicity, they still triggered immune responses in vivo resulting in the reduced yields of transduced cells.

To develop less immunogenic vectors, third generation of adenoviral vectors were developed. These are also termed high-capacity adenoviral vectors (HC-AdVs), also known as gutless AdVs or helper-dependent AdVs (HD-AdVs). The HC-AdV is stripped of all viral coding sequences, resulting in a vector with only 5' and 3' ITRs in addition to a packaging signal, thus providing a larger capacity for transgenic cloning sequences (36 kb). Furthermore, the structure of the HC-AdV minimizes cytotoxicity, thus enabling prolonged expression of therapeutic genes, rendering the HC-AdV the most promising AdV to use for gene therapy to date. HC-AdVs are beneficial because they lack the viral elements that can cause an immune response in the host. HC-AdV's are deemed "helper-dependent" because while these vectors lack viral genetic components, they also lack the necessary packaging components. A complementary virus, or helper virus (HV), can be used to provide the necessary proteins in trans for the packaging of an Ad-based vector. The HV is not packaged along with the desired HC-AdV because it has its packaging sequences flanked by loxP recognition sites, which is sufficiently excised by Cre recombinase so that the helper virus DNA remains unpackaged. While the packaging ability of the HV is stunted, the HV is replicated at normal levels and can thus express all of the functions necessary in trans for replication and packaging of a vector genome containing the appropriate cis-acting elements.

The generation of recombinant adenoviral vectors and the generation of the required recombinant adenoviral genomes has been described in detail by Lee et al (Genes Dis. 2017 June; 4(2): 43-63. doi: 10.1016/j.gendis.2017.04.001) and the required techniques are known to the person skilled in the art. Generation of such adenoviral genomes is also evident from the description of the examples below.

At least four commonly used methods to generate and produce adenovirus vectors for gene delivery have been developed, which all require linearization of the recombinant adenoviral genome. The first, traditional method uses recombination in HEK-293 cells. The gene of interest (GOI) is first cloned into a shuttle vector, which contains 5'-ITR, packaging signal and homologous regions to adenoviral genome. Adenoviruses are generated in HEK-293 cells through recombination between shuttle vector, which has to be linearized prior to transfection into the producing cells, and adenoviral backbone vector, which is unable to produce virus by itself. A second approach uses Cre/LoxP-mediated recombination. The GOI is cloned into a shuttle vector that contains LoxP site(s). Cre recombinase-mediated recombination occurs with a LoxP-containing adenoviral backbone vector in vitro or 293-Cre cells, leading to the generation of adenoviruses. A third approach uses the AdEasy system. The GOI is subcloned into a shuttle vector that contains 5'-ITR and packaging signal, as well as a kanamycin-containing bacterial replication unit flanked with homologous arms. Recombinant adenoviral plasmids are generated through homologous recombination between the linearized shuttle vector and ampicillin-resistant adenoviral backbone vector, such as pAdEasy1, in the bacterial strain BJ5183 cells under kanamycin selection. The resultant adenoviral plasmids are linearized and used for adenovirus production in HEK-293 cells. A fourth approach uses helper adenovirus for the production of HC-AdVs (or HD-AdVs, or Gutless AdVs). The GOI is cloned into a transfer vector that contains both ITRs and packaging signal only. Adenoviruses are generated with a helper adenovirus, which will not be packaged due to the deletion of packaging signal in the modified HEK-293 cells, usually through Cre/LoxP or FLP/FRT excision system.

The term "recombinant" adenoviral genome refers to the fact that the genomic DNA sequences of the adenoviral genome comprised by the circular DNA molecule of the invention is formed or assembled by laboratory methods of genetic recombination, such as molecular cloning, to bring together genetic material from multiple sources, creating sequences that would not otherwise be found. Additionally, in the context of adenoviral genomes it is understood that the term also refers to viral genomes resulting from recombination between virus genomes in a cell infected by more than one virus strain, which can occur by homologous recombination of the nucleic acid strands of the genomes of the different virus strains.

With respect to the term "cells suited for rescuing recombinant adenoviruses", it is understood that it relates to cells or cell lines that have been found to be useful for generation of viral particles after delivery of the sequence of the recombinant adenoviral genome and potentially other components for generating recombinant adenoviral particles. Accordingly, such cells are also referred to as producer cells/cell lines or producing cells/cell lines.

As explained herein and known to the skilled person, adenoviral vectors (also referred to as adenoviral particles), in particular those of the HAdV-5, are highly attractive for a wide range of gene therapy, vaccine and virotherapy applications. Wild type HAdV-5 virus can replicate in numerous tissue types. However, to use Ad vectors for therapeutic purposes the viral genome requires modifications, as described herein and know in the art. If the viral genome is modified in such a way that the viral life cycle is interfered with, a specific producer cell line is required to provide trans-complementation to overcome the modification and allow viral production. Depending on the type of adenoviral vector and the recombinant viral genome, a skilled person can select suitable cells lines for producing the adenoviral particles.

Provision of trans-complementation can occur in two ways; use of a producer cell line that contains specific adenoviral sequences incorporated into the cell genome to trans-complement, or use of a producer cell line that naturally complements for the modified Ad vector genome. Suitable cell lines are known in the art and can be identified by a skilled person, for example based on review articles such as Kovesdi et al. (Viruses. 2010 August; 2(8): 1681-1703. doi: 10.3390/v2081681). Suitable cell lines for use in the context of the invention are disclosed in the examples below.

For example, when the E1 region of the genome is replaced with an expression cassette to produce the gene product that is useful in therapy (such as suicide genes, antigens and antibodies), a producer cell line containing adenovirus E1 sequences is required to complement for this region. In contrast, the E3 region, which encodes products that counteract host defense mechanisms, is dispensable and not essential for viral replication in vitro, so it is not necessary to trans-complement for E3. To trans-complement for the lack of E1 the historic cell line has been HEK293. The human embryonic kidney (HEK) 293 cell line was developed over 30 years ago through an insertion of E1A and E1B sequence, from nucleotides (nt) 1 to 4344, into chromosome 19 at 19q13.2. An alternative producing cell line (also called producer cell line) is the 911 cell line generated by incorporation of Ad5 nt 79-5789 into the genome of human embryonic retinoblasts (HER) cells through plasmid transfection. The 911 cell line was determined to outperform HEK293 in plaque formation and attainment of yields and consequently became another favored cell line. The A549 cell line is a Lung Carcinoma Cell Line and has been found to be suitable for adenovirus production, most notably replicating adenovirus constructs that do not require complementation by the viral oncogene, early region 1A (E1A), which is responsible for viral gene transcription. This cell line is further utilized as a negative control in assays to measure the replication of adenoviruses that lack E1A and as a target cell line to detect replication competent adenoviruses (RCA).

It is one of the great advantages of the present invention that linearization of the circular dsDNA molecule comprising the recombinant adenoviral genome does not have to occur prior to transfection of the dsDNA into the producing cells, but it can occur inside the producing cells through cleavage/generation of double strand breaks bey the CRISPR/Cas system. Linearization inside the cell is highly advantageous since like this circular DNA can be transfected, which much easier and more efficient than the transfection of linearized DNA. Furthermore, the step of linearization occurs automatically inside the cell via CRISPR/Cas technology. As used herein, "linearization" refers to the induction of at least one double strand break in a circular DNA molecule. In embodiments, more than one DSB can be generated in the circular DNA molecule, resulting in a linear DNA molecule comprising the recombinant adenoviral genome. This is in particular the case, when both ITRs of the recombinant adenoviral genome in the circular dsDNA molecule are associated with a target sequence adjacent to a PAM sequence configured for generating an RNA-guided DNA endonuclease-mediated DNA double strand break at the external end of or in close proximity outside the external end of each of the two ITRs.

The circular DNA molecule of the invention comprising the recombinant adenoviral genome can be any suitable kind of circular DNA molecule, such as preferably a bacterial artificial chromosome (BAC) or a plasmid, preferably a high copy plasmid.

Adenoviral vectors can have large genomes (i.e. 36 kb) making genetic manipulations by classical cloning strategies difficult and ineffective. However, there are virus cloning technologies using BACs that benefit from the large cloning capacity of BACs. A bacterial artificial chromosome (BAC) is a DNA construct, based on a functional fertility plasmid (or F-plasmid), used for transforming and cloning in bacteria, usually *E. coli*. F-plasmids play a crucial role because they contain partition genes that promote the even distribution of plasmids after bacterial cell division. The bacterial artificial chromosome's usual insert size is 150-350 kbp. A similar cloning vector called a PAC has also been produced from the DNA of P1 bacteriophage and can also be used in embodiments of the invention.

Plasmids are circular DNA molecules. Inside a cell, plasmids are physically separated from chromosomal DNA and can replicate independently. They are most commonly found as small circular, double-stranded DNA molecules in bacteria; however, plasmids are sometimes present in archaea and eukaryotic organisms. In nature, plasmids often carry genes that benefit the survival of the organism and confer selective advantage such as antibiotic resistance. While chromosomes are large and contain all the essential genetic information for living under normal conditions, plasmids are usually comparably small and contain only additional genes that may be useful in certain situations or conditions.

As used herein the circular DNA molecules of the invention can be considered artificial plasmids. Artificial plasmids in general are widely used as vectors in molecular cloning, serving to drive the replication of recombinant DNA sequences within host organisms. In the laboratory, plasmids may be introduced into a cell via transformation. In order for plasmids to replicate independently within a cell, they must possess a stretch of DNA that can act as an origin of replication. The self-replicating unit, in this case, the plasmid, is called a replicon. A typical bacterial replicon may consist of a number of elements, such as the gene for plasmid-specific replication initiation protein (Rep), repeating units called iterons, DnaA boxes, and an adjacent AT-rich region. Smaller plasmids make use of the host replicative enzymes to make copies of themselves, while larger plasmids may carry genes specific for the replication of those plasmids. A few types of plasmids can also insert into the host chromosome, and these integrative plasmids are sometimes referred to as episomes in prokaryotes. Artificially constructed plasmids may be used as vectors in genetic engineering. These plasmids serve as important tools in genetics and biotechnology, where they are commonly used to clone and amplify (make many copies of) or express particular genes. A wide variety of plasmids are commercially available for such uses, and multiple kind of plasmids and circular DNA molecules for cloning recombinant adenoviral genomes and used in methods for rescuing adenoviral vectors from producing cells have been described.

As used herein, the process of generating, preferably collecting and optionally isolating/purifying recombinant adenoviral particles in a producing cell line is referred to as "rescue of recombinant adenoviruses". This involves the introduction of the circular DNA into a suitable producing cell line, the linearization of the circular DNA by cutting of a RNA-guided endonuclease just outside or in close proximity outside of one, preferably both ITRs, and the subsequent collection of viral particles from the supernatant of the producing cells. Collection of viral particles from cell culture is a routine procedure involving collection of the cell supernatant, and preferably separating cells from the liquid containing viral particle, for example by filtering or centrifugation. The viral particles can be quantified by routine techniques known in the art and can be further concentrated by ultracentrifugation, for example.

CRISPR is an abbreviation of Clustered Regularly Interspaced Short Palindromic Repeats and is a family of DNA sequences in bacteria. The sequences contain snippets of DNA from viruses that have attacked the bacterium. These snippets are used by the bacterium to detect and destroy DNA from further attacks by similar viruses. These sequences play a key role in a bacterial defense system and form the basis of a technology known as CRISPR/Cas that effectively and specifically changes genes within organisms.

Sequences of the CRISPR loci are transcribed and processed into CRISPR RNAs (crRNAs) which, together with a trans-activating crRNAs (tracrRNAs), complex with CRISPR-associated (Cas) proteins to dictate specificity of DNA cleavage by Cas nucleases through Watson-Crick base pairing between nucleic acids (Wiedenheft, B et al (2012). Nature 482: 331-338; Horvath, P et al (2010). Science 327: 167-170; Fineran, P C et a. (2012). Virology 434: 202-209).

It was shown that the three components required for the type II CRISPR nuclease system are the Cas9 protein, the mature crRNA and the tracrRNA, which can be reduced to two components by fusion of the crRNA and tracrRNA into a single guide RNA (sgRNA) and that re-targeting of the Cas9/sgRNA complex to new sites could be accomplished by altering the sequence of a short portion of the gRNA (Garneau, J E et al (2010). Nature 468: 67-71; Deltcheva, E et al. (2011). Nature 471: 602-607, Jinek, M et al (2012) Science 337: 816-821).

CRISPR-Cas systems are RNA-guided adaptive immune systems of bacteria and archaea that provide sequence-specific resistance against viruses or other invading genetic material. This immune-like response has been divided into two classes on the basis of the architecture of the effector module responsible for target recognition and the cleavage of the invading nucleic acid (Makarova K S et al. Nat Rev Microbiol. 2015 November; 13(11):722-36.). Class 1 comprises multi-subunit Cas protein effectors and Class 2 consists of a single large effector protein. Both Class 1 and 2 use CRISPR RNAs (crRNAs) to guide a Cas nuclease component to its target site where it cleaves the invading nucleic acids. Due to their simplicity, Class 2 CRISPR-Cas systems are the most studied and widely applied for genome editing. The most widely used CRISPR-Cas system is CRISPR-Cas9.

It was demonstrated that the CRISPR/Cas9 system could be engineered for modification of double stranded DNA molecules inside a cell, for example efficient genetic in mammalian cells. The only sequence limitation of the CRISPR/Cas system appears to derive from the necessity of a protospacer-adjacent motif (PAM) located immediately 3' to the target sequence. The PAM sequence is specific to the species of Cas9. For example, the PAM sequence 5'-NGG-3' is necessary for binding and cleavage of DNA by the commonly used Cas9 from *Streptococcus pyogenes*. However, Cas9 variants with novel PAMs have been and may be engineered by directed evolution, thus dramatically expanding the number of potential target sequences. Cas9 complexed with the crRNA and tracrRNA undergoes a conformational change and associates with PAM motifs throughout the genome interrogating the sequence directly upstream to determine sequence complementarity with the gRNA. The formation of a DNA-RNA heteroduplex at a matched target site allows for cleavage of the target DNA by the Cas9-RNA complex. These methods and mechanisms are well known in the art.

As known in the art, CRISPR/Cas9 has been exploited to develop potent tools for genome manipulation in animals, plants and microorganisms, but, as shown herein, can also be exploited for manipulation of exogenous DNA molecules that have been introduced into a host cell. The RNA-guided Cas9 endonuclease first recognizes a 2- to 4-base-pair conserved sequence named the protospacer-adjacent motif (PAM), which flanks a target DNA site. Upon binding to the PAM, Cas9 interrogates the flanking DNA sequences for base-pairing complementarity to a guide RNA. If there is complementarity between the first 12 base pairs (the 'seed' sequence) of the guide RNA and the target DNA strand, RNA strand invasion accompanies local DNA unwinding to form an R-loop. Precise cleavage of each DNA strand by the RuvC and HNH domains of Cas9 generates a blunt double-strand DNA (dsDNA) break (DSB) at a position three base pairs upstream of the 3' edge of the protospacer sequence, measuring from the PAM.

This DSB inducing activity of Cas9 as a preferred RNA-guided DNA endonuclease is exploited by the present invention for generating DSB in the circular DNA molecule of the invention after introduction into a producing cell comprising suitable gRNA and Cas9.

CRISPR/Cas9 genome-editing experiments have been exploiting the host cell machinery to repair the genome precisely at the site of the Cas9-generated DSB. Mutations can arise either by non-homologous end joining (NHEJ) or homology-directed repair (HDR) of DSBs. NHEJ can produce small insertions or deletions (INDELs) at the cleavage site, whereas HDR uses a native (or engineered) DNA template to replace the targeted allele with an alternative sequence by recombination. Additional DNA repair pathways such as single-strand annealing, alternative end joining, microhomology-mediated joining, mismatch and base- and nucleotide-excision repair can also produce genome edits.

Cas9 variants derived from the *Streptococcus pyogenes* Cas9 (SpCas9) have been generated for use as nickases, dual nickases or FokI fusion variants. More recently, Cas9 orthologs, and other nucleases derived from class 2 CRISPR-Cas systems including Cpf1 and C2c1, have been added to the CRISPR toolbox. These ongoing efforts to mine the abundant bacterial and archaeal CRISPR-Cas systems should increase the range of molecular tools available to researchers.

In the context of the present invention, the term "RNA-guided DNA endonuclease" refers to DNA endonucleases that interact with at least one RNA-Molecule. In the context of the present invention the terms RNA-guided DNA endonuclease and RNA-guided endonuclease are used interchangeably. DNA endonucleases are enzymes that cleave the phosphodiester bond within a DNA polynucleotide chain. In case of RNA-guided DNA endonuclease, the interacting RNA-molecule may guide the RNA-guided DNA endonuclease to the site or location in a DNA where the endonuclease becomes active. In particular, the term RNA-guided DNA endonuclease refers to naturally occurring or genetically modified Cas nuclease components or CRISPR-Cas systems, which include, without limitation, multi-subunit Cas protein effectors of class 1 CRISPR-Cas systems as well as single large effector Cas proteins of class 2 systems.

Details of the technical application of CRISPR/Cas systems and suitable RNA-guided endonuclease are known to the skilled person and have been described in detail in the literature, as for example by Barrangou R et al. (Nat Biotechnol. 2016 Sep. 8; 34(9):933-941), Maeder M L et al. (Mol Ther. 2016 March; 24(3):430-46) and Cebrian-Serrano A et al. (Mamm Genome. 2017; 28(7): 247-261). The present invention is not limited to the use specific RNA-guided endonucleases and therefore comprises the use of any given RNA-guided endonucleases in the sense of the present invention suitable for use in the method described herein.

Any RNA-guided DNA endonuclease known in the art may be employed in accordance with the present invention. RNA-guided DNA endonuclease comprise, without limitation, Cas proteins of class 1 CRISPR-Cas systems, such as Cas3, Cas8a, Cas5, Cas8b, Cas8c, Cas10d, Cse1, Cse2, Csy1, Csy2, Csy3, GSU0054, Cas10, Csm2, Cmr5, Csx11, Csx10 and Csf1; Cas proteins of class 2 CRISPR-Cas systems, such as Cas9, Csn2, Cas4, Cpf1, C2c1, C2c3 and C2c2; corresponding orthologous enzymes/CRISPR effectors from various bacterial and archeal species; engineered CRISPR effectors with for example novel PAM specificities, increased fidelity, such as SpCas9-HF1/eSpCas9, or altered functions, such as nickases. Particularly preferred RNA-guided DNA endonuclease of the present invention are *Streptococcus pyogenes* Cas9 (SpCas9), *Staphylococcus aureus* Cas9, *Streptococcus thermophilus* Cas9, *Neisseria meningitidis* Cas9 (NmCas9), *Francisella novicida* Cas9 (FnCas9), *Campylobacter jejuni* Cas9 (CjCas9), Cas12a (Cpf1) and Cas13a (C2C2) (Makarova K S et al. (November 2015). Nature Reviews Microbiology. 13 (11): 722-36).

The definition and explanations provided herein are mainly focused on the SpCas9 Crispr/Cas system. However, the person skilled in the art is aware of how to use alternative Crispr/Cas systems as well as tools and methods that provide or allow the gain of information on the details of such alternative systems.

In embodiments, the DNA molecule of the invention can be configured for generation of DSB mediated by a different RNA-guided endonuclease than Cas9 or SpCas9, such as for example Cpf1. Cpf1 requires one associated guide RNA for generating staggered/sticky end cuts and it cuts in non-dividing cells, such as nerve cells.

The RNA-guided DNA endonuclease and in particular Cas9 may also be a modified protein, wherein the nuclease function of the protein is altered into a nicking endonuclease function, which only cuts one of the two DNA strands of the dsDNA. In other words, the naturally occurring endonucleases function of cleaving both strands of a double-stranded target DNA, is altered into an endonuclease that cleaves (i.e. nicks) only one of the strands. Such modified RNA-guided DNA endonucleases are also called "nickases" in the context of the present invention. Means and methods of modifying RNA-guided DNA endonuclease such as Cas9 accordingly are well known in the art and include for example the introduction of amino acid replacements into Cas9 that render one of the nuclease domains inactive. More specifically, aspartate can be replaced against alanine at position 10 of the *Streptococcus pyogenes* Cas9 (SpCas9 D10A; Cong et al. (2013) Science 339:819-823). Further examples are known in the art, for example the H840A replacement in SpCas9 (Mali P et al. Nat Biotechnol. 2013 September; 31(9):833-8; Ran F A et al. Cell. 2013 Sep. 12; 154(6):1380-9).

In accordance with the method of the invention, the RNA-guided DNA endonuclease may be introduced as a protein, but alternatively the RNA-guided DNA endonuclease may also be introduced in form of a nucleic acid molecule encoding said protein. It will be appreciated that the nucleic acid molecule encodes said RNA-guided DNA endonuclease in expressible form such that expression in the cell results in a functional RNA-guided DNA endonuclease protein such as Cas9 protein. Means and methods to ensure expression of a functional polypeptide are well known in the art.

For example, the coding sequences for the endonuclease may be comprised in a vector, such as for example a plasmid, cosmid, virus, bacteriophage or another vector used conventionally e.g. in genetic engineering. The coding sequences inserted in the vector can e.g. be synthesized by standard methods or isolated from natural sources. The coding sequences may further be ligated to transcriptional regulatory elements and/or to other amino acid encoding sequences. Such regulatory sequences are well known to those skilled in the art and include, without being limiting, regulatory sequences ensuring the initiation of transcription, internal ribosomal entry sites (IRES) and optionally regulatory elements ensuring termination of transcription and stabilization of the transcript. Non-limiting examples for regulatory elements ensuring the initiation of transcription comprise a translation initiation codon, transcriptional enhancers such as e.g. the SV40-enhancer, insulators and/or promoters, such as for example the cytomegalovirus (CMV) promoter, SV40-promoter, RSV-promoter (Rous sarcome virus), the lacZ promoter, chicken beta-actin promoter, CAG-promoter (a combination of chicken beta-actin promoter and cytomegalovirus immediate-early enhancer), the gai10 promoter, human elongation factor 1a-promoter, A0X1 promoter, GAL1 promoter CaM-kinase promoter, the lac, trp or tac promoter, the lacUV5 promoter, the *Autographa californica* multiple nuclear polyhedrosis virus (AcMNPV) polyhedral promoter or a globin intron in mammalian and other animal cells. Non-limiting examples for regulatory elements ensuring transcription termination include the V40-poly-A site, the tk-poly-A site or the SV40, lacZ or AcMNPV polyhedral polyadenylation signals, which are to be included downstream of the nucleic acid sequence of the invention. Additional regulatory elements may include translational enhancers, Kozak sequences and intervening sequences flanked by donor and acceptor sites for RNA splicing. Moreover, elements such as origin of replication, drug resistance gene or regulators (as part of an inducible promoter) may also be included.

Nucleic acid molecules encoding said RNA-guided DNA endonuclease include DNA, such as cDNA or genomic DNA, as well as RNA and in particular mRNA. It will be readily appreciated by the skilled person that more than one nucleic acid molecule may encode an RNA-guided DNA endonuclease in accordance with the present invention due to the degeneracy of the genetic code. Degeneracy results because a triplet code designates 20 amino acids and a stop codon. Because four bases exist which are utilized to encode genetic information, triplet codons are required to produce at least 21 different codes. The possible e possibilities for bases in triplets give 64 possible codons, meaning that some degeneracy must exist. As result, some amino acids are encoded by more than one triplet, i.e. by up to six. The degeneracy mostly arises from alterations in the third position in a triplet. This means that nucleic acid molecules having different sequences, but still encoding the same RNA-guided DNA endonuclease, can be employed in accordance with the present invention.

The nucleic acid molecules used in accordance with the present invention may be of natural as well as of (semi) synthetic origin. Thus, the nucleic acid molecules may, for example, be nucleic acid molecules that have been synthesized according to conventional protocols of organic chemistry. The person skilled in the art is familiar with the preparation and the use of said probes (see, e.g., Sambrook and Russel "Molecular Cloning, A Laboratory Manual", Cold Spring Harbor Laboratory, N.Y. (2001)).

The present invention relates to the generation of double strand beaks of the circular dsDNA molecule. Therein, the circular DNA molecule of the invention comprises at least one, preferably two target sequences, which are associated with an ITR and which are targeted by the at least one guide RNA associated with an RNA-guided DNA endonuclease.

In accordance with the present invention, a "target sequence" is a nucleotide sequence in the dsDNA molecule that is recognized by the at least one guide RNA that is associated with the RNA-guided endonuclease due to the target specific sequence comprised by the guide RNA. The target sequence is at least partially complementary to the target specific sequence of the guide RNA and is associated with a so-called protospacer adjacent motif (PAM). The PAM is a 2-6 base pair DNA sequence located adjacent to the target sequence and can be located either at the 5'-end (for example for the Crispr/Cpf1 system) or at the 3'-end of the target sequence (for example for the Crispr/Cas9 system), depending on the Crispr/Cas system employed. An RNA-guided endonuclease, such as Cas9 or Cpf1, will not successfully bind to and cleave the targeted dsDNA molecule if the recognized target sequence is not associated with a PAM sequence. The formation of a DNA-RNA heteroduplex between the target sequence and the target specific sequence of the guide RNA allows for cleavage of the target DNA by the guide RNA/RNA-guided endonuclease complex. Cleavage of the targeted dsDNA molecule occurs within the target sequence or at a site adjacent to the target sequence, depending on the used RNA-guided endonuclease and CRISPR/Cas system.

For example, in case of SpCas9 the DNA target sequence of at least 20 nucleotides is located directly upstream/at the 5'-end of an invariant 5'-NGG-3' PAM. Accordingly, in case SpCas9 is used as a RNA-guided endonuclease, it is understood that a target sequence located adjacent to a PAM means that the target sequence starts directly upstream from the PAM sequence, without further nucleotides in between. Correct pairing of the guide RNA to the DNA target sequence leads to the generation of a double strand break in the dsDNA molecule ("cleavage" of the dsDNA molecule by SpCas9) 3 base-pairs (bp) upstream of the PAM within the target sequence.

However, if for example the CRISPR/Cpf1 system is used, the Cpf1-crRNA complex cleaves target DNA by identification of a target sequence that may be located downstream/at the 3' end of a protospacer adjacent motif (for example 5'-YTN-3' (where "Y" is a pyrimidine and "N" is any nucleobase) or 5'-TTN-3'). Cpf1 can introduce a sticky end/staggered end DNA double strand breaks. In case of AsCpf1 and LbCpf1 a double strand break with a 4 nucleotides overhang can be generated, which can occur 19 bp downstream of the PAM on the targeted (+)-strand and 23 bp downstream of the PAM on the (−)-strand.

As illustrated by the above examples, the exact site of the double strand break depends on the Crispr/Cas system or the RNA-guided endonuclease employed in the method of the invention and can therefore be determined by the person skilled in the art upon selection of the RNA-guided endonuclease.

In the context of the present invention, the target sequence may also be called "protospacer". The term "target site" may refer to a location or sequence in the dsDNA molecule comprising the target sequence and an associated PAM.

In the context of the present invention, the term "double strand break" or "DSB" refers to interruption of both strands of a dsDNA molecule leading to the separation of the parts of the dsDNA molecule that lie upstream and downstream of the side of the double strand break. In contrast, a single strand break refers to the interruption of only one of the two DNA strands and will not lead to a separation of the parts of the dsDNA molecule that lie upstream and downstream of the side of the double strand break.

In preferred embodiments, the RNA-guided endonuclease generates blunt ends. In alternative embodiments, the RNA-guided endonuclease generates sticky ends.

In the context of the present invention, double strand breaks can occur due to cleavage of both strands by one RNA-guided endonuclease or due to two single-strand cuts on both the (+)- and the (−)-strand by nickases.

A double strand break can be generated by cleavage of both strands of the dsDNA at the same/corresponding position on the complementary strands, leading to the formation of blunt ends of the resulting separated ends of the dsDNA molecule, as it is mostly the case for Cas9 mediated cleavage. However, in case of non-canonical cleavage, Cas9 may also induce the formation of double strand breaks with sticky/staggered ends, wherein the strand breaks on the two complementary DNA strands of the dsDNA are located at different positions, leading to the formation of strand-overhangs on the ends of the cleaved dsDNA molecule.

Furthermore, certain RNA-guided endonucleases regularly generate sticky ends, such as for example Cpf1. It is also possible to influence the tendency of RNA-guided endonucleases to generate sticky-ends or blunt ends through selection of certain target sequence.

Additionally, it is possible to intentionally generate sticky ended double strand breaks of a certain configuration by inducing single strand breaks on both the (+)- and the (−)-strand by individual nickases targeting different target sequences on the two strands. By using this approach, it is possible to precisely select the site of a single strand break.

Induction of two single strand breaks on both complementary strands within a distance of no more than 50 nucleotides, preferably not more than 40 nt, 35 nt, 30 nt or 25, most preferably not more than 20, 19, 18, 17, 16, 15 14, 13, 12, 11, 10, 9, 8, 7, 6, 5, 4, 3, 2 or 1 nt will lead to a separation of the ends of the dsDNA molecule that are distal and proximal of the corresponding single strand breaks, resulting in the formation of stick ends with overhangs of the corresponding length. By using this approach of inducing a double strand break, it can be precisely selected what kind of overhang at the resulting separated ends of the dsDNA molecule is generated. For each double strand break, at least two guide RNA molecules may be required.

It is understood that the term "expression cassette" refers to a distinct component of vector DNA consisting of a coding sequence, such as a gene, and regulatory sequence to be expressed by a transfected cell. In each successful transformation, the expression cassette directs the cell's machinery to make (express) RNA and eventually protein(s), depending on the kind of expression cassette. There are expression cassettes comprising regulatory sequences for protein expression and those that are specific for expression of certain kinds of RNA. Some expression cassettes are designed for modular cloning of RNA- or protein-encoding sequences so that the same cassette can easily be altered to make different RNAs or proteins. For example, an expression cassette can be composed of one or more genes or coding sequences and the sequences controlling their expression. Preferably, an expression cassette comprises three components: a promoter sequence, an open reading frame, and a 3' untranslated region that, in eukaryotes, usually contains a polyadenylation site. Different expression cassettes can be transfected into different organisms including bacteria, yeast, plants, and mammalian cells as long as the correct regulatory sequences are used.

In embodiments of the invention, the circular DNA molecule comprises expression cassettes for one or more gRNAs and/or for Cas9. Such expression cassettes are located between the two ITRs of the recombinant adenoviral genome outside the adenoviral genome sequence, i.e. in the backbone of the circular DNA molecule. Such embodiments are preferable embodiments where the recombinant adenoviral genome is comprised by a BAC, since a BAC is large enough to additionally harbor the expression cassettes for one or two or more gRNA and/or Cas9 or another suitable RNA-guided endonuclease.

In embodiments of the invention, expression cassettes for expression one, two or more gRNAs and/or for expression of Cas9 are present in the producing cells in DNA molecules that are different from the circular DNA molecule comprising the recombinant adenoviral genome. For example, such expression cassettes may be introduced on different plasmids or have been introduced by means of a viral vector. The expression cassettes may have been integrated into the genome of the producing cell. Suitable regulators sequences, such as promoter and/or enhancer sequences for mediating expression of gRNA and Cas9 are known in the art, and specific examples of such regulatory sequences are described in the example section below.

In embodiments, the gRNA and Cas9 may also be introduced into the cell by RNA or protein transfection or other methods described in the art for providing these components of the CRISPR/Cas system.

The present invention also relates to an in vitro method for rescuing recombinant adenoviruses, the method comprising a. providing cells suited for rescuing recombinant adenoviruses, such as 293 cells,
b. introducing into said cell a circular DNA molecule of the invention comprising a recombinant adenoviral genome with two inverted terminal repeats (ITRs) flanking the genome ends, wherein at least one of the ITRs is associated with a target sequence adjacent to a PAM sequence, wherein each of the target sequences is configured for generating an RNA-guided DNA endonuclease-mediated DNA double strand break at the external end of or in close proximity outside the external end of the respective ITR,
c. providing inside the cell an RNA-guided DNA endonuclease and at least one gRNA for targeting the RNA-guided DNA endonuclease to the target sequence of the circular DNA molecule,
d. linearizing recombinant adenoviral genome comprising the two ITRs inside the cells,
e. collecting viral particles from the cell supernatant.

The term "introducing into the cell", as used herein, relates to any known method of bringing a protein or a nucleic acid molecule into a cell. Provision of a protein, such as an RNA-guided DNA endonuclease, or a nucleic acid molecule inside a cell can be achieved by previous introduction of said molecule itself or by introduction of another molecule enabling expression of said molecule. Non-limiting examples of methods of introducing a molecule into a cell include microinjection, infection with viral vectors, electroporation, transfection, such as transfection using formulations with cationic lipids. Suitable methods for introducing the components of the present invention into a cell are known to the skilled person. In embodiments, the method of the invention comprises introducing into a producing cell a nucleic acid molecule encoding an RNA-guided DNA endonuclease and/or at least one guide RNA.

As used herein "nucleic acid" shall mean any nucleic acid molecule, including, without limitation, DNA, RNA and hybrids or modified variants thereof. An "exogenous nucleic acid" or "exogenous genetic element" relates to any nucleic acid introduced into the cell, which is not a component of the cells "original" or "natural" genome. Exogenous nucleic acids may be integrated or nonintegrated in the genetic material of the target cell, or relate to stably transduced nucleic acids.

The nucleic acid molecules used in accordance with the invention may be nucleic acids mimicking molecules known in the art such as synthetic or semi-synthetic derivatives of nucleic acid molecules and mixed polymers. They may contain additional non-natural or derivatized nucleotide bases, as will be readily appreciated by those skilled in the art. Nucleic acid mimicking molecules or nucleic acid derivatives according to the invention include, without being limiting, phosphorothioate nucleic acid, phosphoramidate nucleic acid, morpholino nucleic acid, hexitol nucleic acid (HNA), peptide nucleic acid (PNA) and locked nucleic acid (LNA).

Furthermore, the method of the present invention comprises introducing into the cell at least one guide RNA. In the context of the present invention, a "guide RNA" refers to RNA molecules interacting with RNA-guided DNA endonuclease leading to the recognition of the target sequence to be cleaved by the RNA-guided DNA endonuclease. According to the present invention, the term "guide RNA" (or gRNA) therefore comprises, without limitation, target sequence specific CRISPR RNAs (crRNA), trans-activating crRNAs (tracrRNA) and chimeric single guide RNAs (sgRNA).

crRNAs differ depending on the RNA-guided endonuclease and the CRISPR/Cas system but typically contain a target specific sequence of between 20 to 72 nucleotides in length, flanked by two direct repeats (DR) of a length of between 21 to 46 nucleotides. In the case of *S. pyogenes*, the DRs are 36 nucleotides long and the target sequence is 30 nucleotides long. The 3' located DR of the crRNA is complementary to and hybridizes with the corresponding tracr RNA, which in turn binds to the Cas9 protein.

As used herein, the term "trans-activating crRNA (tracr RNA)" refers to a small RNA, that is complementary to and base pairs with a pre-crRNA (3' located DR of the crRNA), thereby forming an RNA dupiex. This pre-crRNA is then cleaved by an RNA-specific ribonuclease, to form a crRNA/tracrRNA hybrid, which subsequently acts as a guide for the endonuclease Cas9, which cleaves the invading nucleic acid.

As described herein, the genes encoding the elements of a CRISPR/Cas system, such as for example Cas9, tracrRNA and crRNA, are typically organized in operon(s) in bacterial genomes. DR sequences functioning together with RNA-guided endonuclease such as Cas9 proteins of other bacterial species may be identified by bioinformatic analysis of sequence repeats occurring in the respective Crispr/Cas operons and by experimental binding studies of Cas9 protein and tracrRNA together with putative DR sequence flanked target sequences.

Preferably, a chimeric single guide RNA sequence comprising such a target sequence specific crRNA and tracrRNA may be employed. Such a chimeric (ch) RNA may be designed by the fusion of a target specific sequence of 20 or more nucleotides (nt) with a part or the entire DR sequence (defined as part of a crRNA) with the entire or part of a tracrRNA, as shown by (Jinek et al. Science 337:816-821). Within the chimeric RNA a segment of the DR and the tracrRNA sequence are complementary able to hybridize and to form a hairpin structure.

In embodiments, the at least one guide RNA of the present invention may also be encoded by a nucleic acid molecule, which is introduced into the cell. The definitions and preferred embodiments recited above with regard to the nucleic acid molecule encoding the endonuclease equally apply to the nucleic acid molecule encoding these RNAs. Regulatory elements for expressing RNAs are known to one skilled in the art, for example a U6 promoter.

The instant disclosure also includes kits, packages and multi-container units containing the material, molecules and components used in the context of the method of the present invention.

FIGURES

The invention is further described by the following figures. These are not intended to limit the scope of the invention but represent preferred embodiments of aspects of the invention provided for greater illustration of the invention described herein.

DETAILED DESCRIPTION OF THE FIGURES

Figures 1A, 1B:
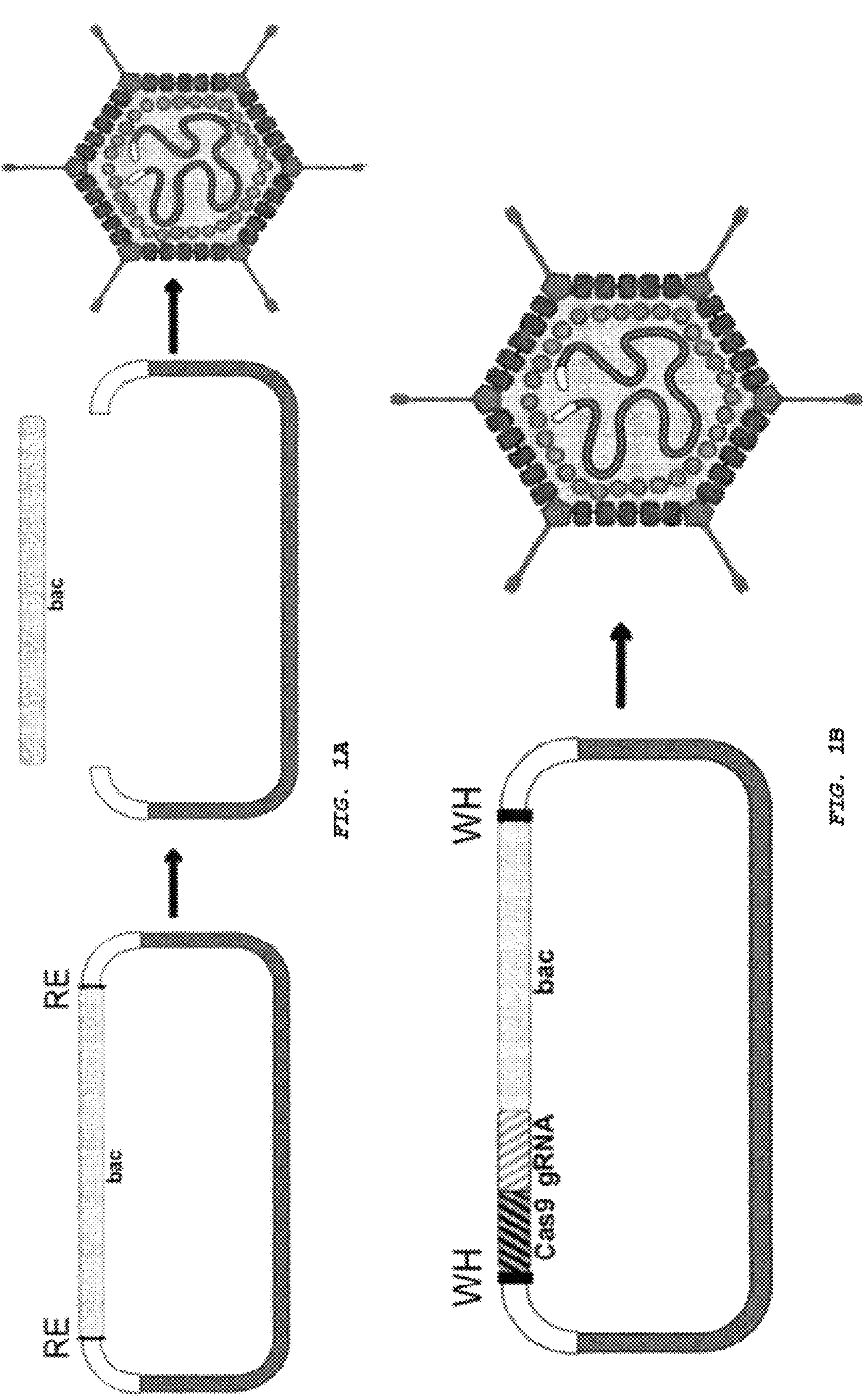
FIG. 1A-C: Schematic representation of linearization strategies of DNA coding for recombinant adenovirus genomes.
Figure 1C:
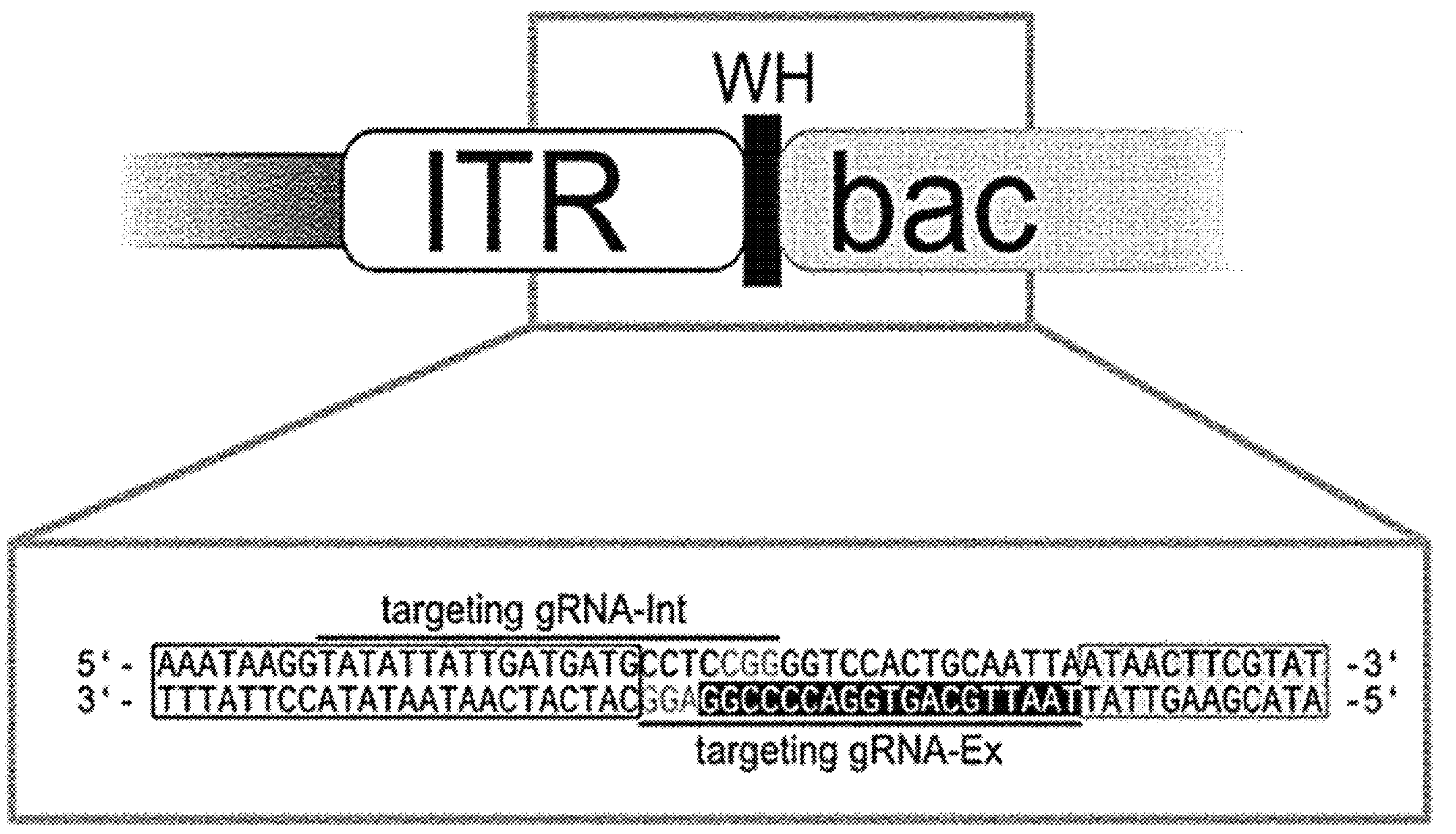

FIG. 1A-C: A) The conventional way of adenovirus reconstitution is by linearizing a circular DNA carrying rAd genome and maintained via a bacterial maintenance cassette (bac) in *E. coli* as plasmid or BAC. The constructs are linearized by treatment of the purified DNA with restriction endonucleases which exclusively recognise sites next to the viral ITRs (RE). The linearized DNA, after an additional purification step, can then be transfected to an appropriated cell to yield replicating viruses. B) The approach tested in this study uses the targeted endonuclease activity of Cas9 in order to facilitate the terminal resolution in vivo. Therefore, the plasmid can be extracted from *E. coli* and directly introduced into the permissive cells. C) To allow in vitro terminal resolution the viral ITRs are extended by the CRISPR/Cas9 target sequence (warhead; WH) and the required PAM (grey letters). The warhead was designed to target a universal sgRNA (gRNA-Ex, indicated by underline) inducing double-strand breaks in the presence of Cas9 6-7 bp from the ITR. Alternatively, the same sequence allows design of sgRNAs (gRNA-Int) that target the ITR which is specific for each adenovirus type. Here the ITR sequence of HAdV-C5 is shown as example. This sgRNA would direct the double-strand breaks in the presence of Cas9 proximal to the genome ends. Displayed are sequence SEQ ID NO. 33 (upper) and corresponding complementary sequence SEQ ID NO. 34 (lower) representing the DNA double strand sequence in the region bridging the outside end of an ITR, the introduced warhead sequence and the neighbouring sequence of the BAC.

FIG. 2A-H: A) Schematic representation of different ways to provide the CRISPR/Cas9-components for terminal resolution. i) Representation of co-transfection by plasmids expressing sgRNA and Cas9 protein with the construct carrying the rAd genome. ii) Depicts one construct coding for the rAd genome and all CRISPR-Cas9-components. iii) The Cas9 is delivered by constitutively expression of the cell line which is used to rescue the rAd, while a plasmid coding for a rAd genome is co-transfected together with a sgRNA-expressing plasmid. iv) The same as iii), but sgRNA is expressed from the same construct coding for the rAd genome. B) Reconstitution efficiency as foci per transfected μg of DNA of HAdV-C5 based rAds, the circular construct pBWH-C5-mChe, after introduction of in vitro endonuclease (Pac) treated rAd genome, a circular Ad genome carrying ITRs adjacent to each other, and co-transfection of pBWH-C5-mChe and pAR-gRNA-Cas9-Amp into 293A C) or pBAd19a-GFP treated in vitro with Pac or pBWH-D64-GFP together with pAR-gRNA-Cas9-Amp. D) Comparison of the efficiency of delivery pathway i and ii (in A) after transfection of 293A cells with the depicted constructs (pBW-C5-mChe-Cas9 and pBWH-C5-mChe together with pAR-gRNA-Cas9-Amp). E) The reconstitution efficiencies of constructs (pBWH-C5-mChe-DD-Cas9) expressing conditional Cas9 (DDD-Cas-9), when applying Shield-1 at indicated concentrations, are compared to a wt Cas9 expressing construct (pBWH-C5-mChe-Cas9) after transfection to 293A as above. F) Comparison of the reconstitution efficiency of warheaded rAd constructs (pAC05-CE-1 or pBWH-C5-mChe) in Cas9 expressing cell line (pathways iii, and iv, as depicted in A) to the basic methodology (depicted as i in A) applied in 293A cells. G) Comparison of the rescue efficiency of pBWH-C5-mChe and pBWH-D64-GFP, respectively, co-transfected with pSG5-Cas9 and a sgRNA targeting the warhead sequences (gRNA-Ex) or the ITRs (gRNA-IntC5 or gRNA-IntD64, respectively). The sgRNA-Ex is targeting the double-strand break 6-7 bp apart from the ITR, while the strain-specific sgRNA-Ints are targeting the double-strand breaks exactly to the 5'-end of the ITR (see FIG. 1C). The focus number was determined Day 4 or 7, respectively, post transfection. H) Comparison of the rescue efficiency of pBWH-C5-mChe with the single ITR-flanked constructs pBWH-L-C5-mChe and pBWH-R-C5-mChe, co-transfected with pAR-gRNA-Amp targeting the warhead sequences (gRNA-Ex) into 293-Cas9 cells. The focus peak formation was determined starting at day 4 post transfection.

Figure 3:
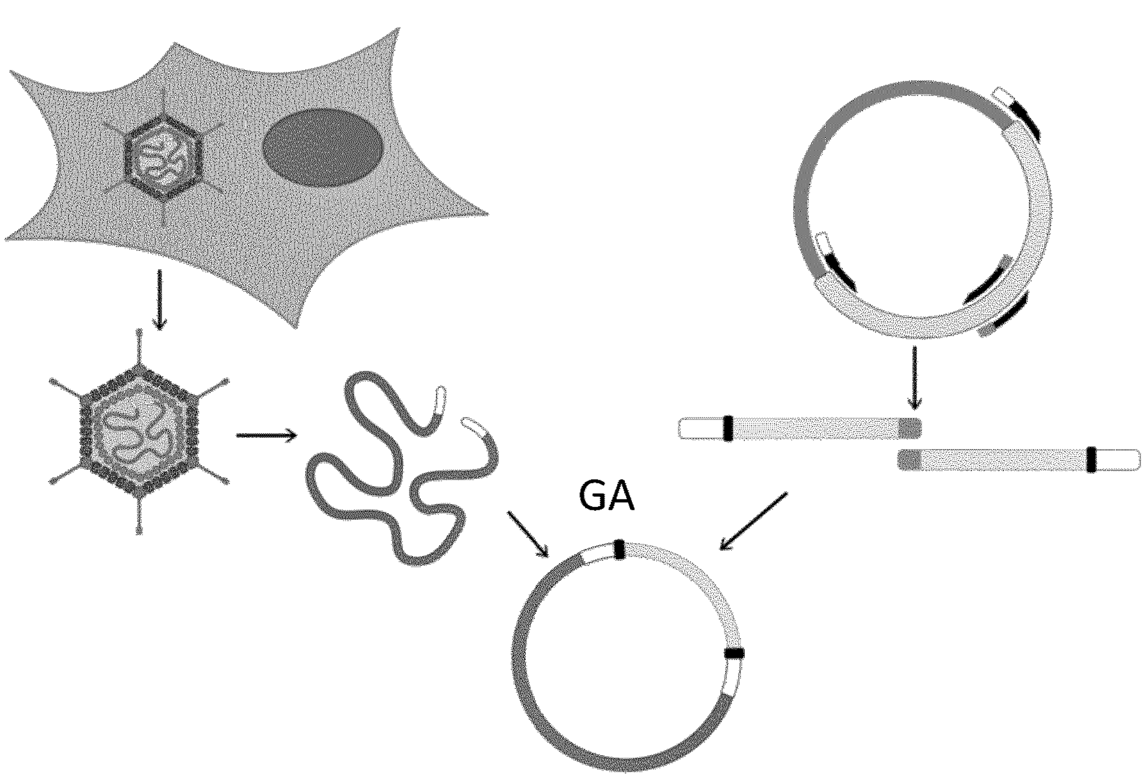
FIG. 3: Schematic representation of the reverse genetic system that uses the CRISPR-Cas9 mediated terminal resolution (CTR) approach.

FIG. 3: Viral DNA (dark grey, flanked with open symbols for ITRs) is extracted from infected cells and the bacterial vector (light grey) is amplified by PCR using two different primer pairs. The external primers of each pair are flanked by homologies (40 nt) to the respective viral ITRs (open symbols) and also includes the warhead sequences (black bars). The two internal primers are flanked with homologies (40 nt) to each other (grey boxes). The viral DNA and the two resulting PCR amplicons can be fused in a Gibson assembly (GA) reaction making it ready for bacterial transformation.

Figure 4:
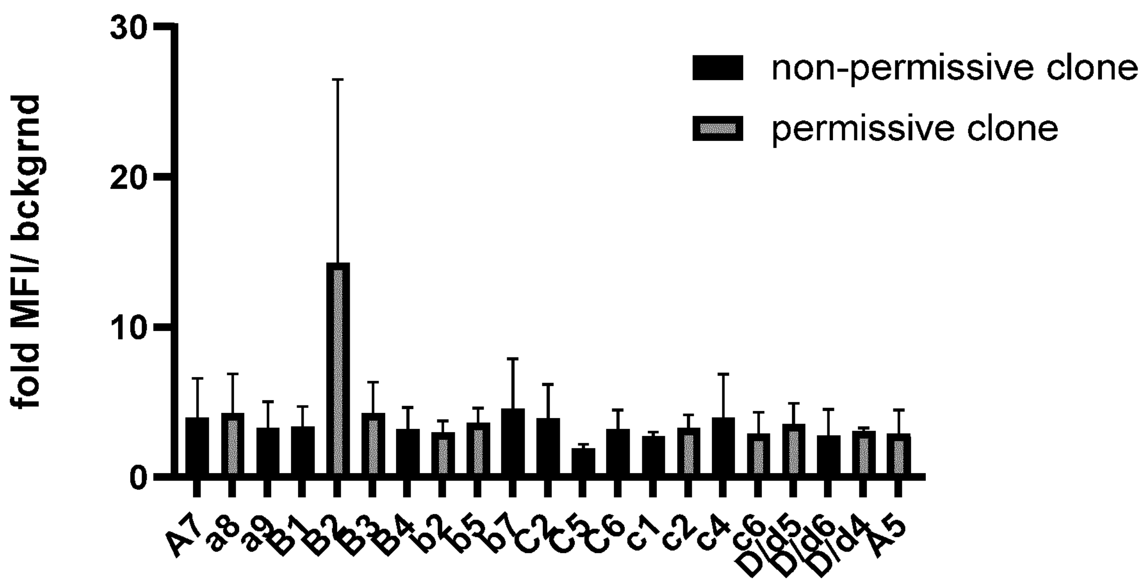
FIG. 4: Relative expression level of Cas9 protein of different 293A-Cas9 cell clones stably transfected with pSG5-Cas9.

FIG. 4: Single clones were picked after stable transfection of 293A cells with pSG-Cas9 under G418 selection. All clones, which could initiate continuous cell lines in the presence of continuous G418 selection, are depicted on the x axis. The Cas9 expression level was determined using flow cytometry detecting the C-terminal Flag-tag on Cas9. The mean fluorescence intensity (MFI) was calculated as fold-change compared to the signal recovered after staining the parental 293A cells. The cell clone B2 was in all three independent experiments the cell line with highest expression level. All clones were additionally tested for their ability to reconstitute HAdC5-mChe after co-transfection of circular pBWH-C5-mChe and pAR-gRNA. The clone was considered to be positive (permissive, grey bars), if it supported rAd foci formation in two independent experiments. The clones, which were not able to support rAd rescue reproducibly were considered non-permissive (black bars).

FIG. 5A-D: A) One of the newly constructed ITR-bacmid borders are shown for the pBWH-C5-mChe which can be targeted by sgRNA-Ex (lower strand, PAM is underlined) inducing double-strand breaks 6-7 bp outside of the ITRs (indicated by the black triangles on the sgRNA targeting strand only). Another sgRNA (sgRNA-IntC5, upper strand, PAM is underlined) targeting the ITRs (bold) can induce Cas9 mediated cleavage directly at the ITRs. To check the impact of cleavage distance, the ITRs were extended using a 12 bp long spacer between the end of the ITRs (see lower panel, Ad5-18/19) and the CRISPR/Cas9 target sequences, which were targeted by sgRNA-Ex (lower strand, PAM is underlined) inducing double-strand breaks (black triangles) 18-19 bp upstream of the ITRs. Displayed are sequence SEQ ID NO. 61 (upper) and corresponding complementary sequence SEQ ID NO. 62 (lower) representing the DNA double strand sequence in the region bridging the outside end of an ITR and the neighbouring sequence of the BAC.B) rAd reconstitution efficiencies were compared after co-transfection of 293A cells with pBWH-C5-mChe and pSG5-Cas9 in the presence of either sgRNA-IntC5 (Ad5-Int5) or sgRNA-Ex (Ad5-Ex), with pBWH18/19-C5-mChe in the presence of either sgRNA-Ex (Ad5-18/19-Ex). The primary rescue efficiencies were obtained as in FIG. 2G). Significance was calculated using Welch ANOVA test. C) Similarly, to the HAdV-5 based constructs above (upper panel), a recombinant HAdV-4 based bacmid was constructed, which was flanked with warhead sequences (PAM is underlined) at both ITRs (here the right ITR is shown, white letters). This sequence can be targeted by the universal sgRNA-Ex like the HAdV-5 based constructs. Here also another sgRNA (sgRNA-Int4, upper strand, PAM is underlined) targeting the HAdV-4 ITRs (bold) can induce Cas9 mediated cleavage directly at the Ad4-ITRs (gray triangles). Displayed are sequence SEQ ID NO. 63 (upper) and corresponding complementary sequence SEQ ID NO. 64 (lower) representing the DNA double strand sequence in the region bridging the outside end of the right ITR and the neighbouring sequence of the BAC. D) The rAd reconstitution efficiencies were determined after co-transfection of 293A cells with pBWH-E4-DE3 with either pAR-gRNA-Ex expressing sgRNA-Ex (E4-Ex) or with pAR-gRNA-lnt4 (E4-Int4) expressing sgRNA-Int4. The primary rescue efficiencies were obtained as in FIG. 2G. Significance was calculated using unpaired t-test.

Examples

The invention is further described by the following examples. These are not intended to limit the scope of the invention but represent preferred embodiments of aspects of the invention provided for greater illustration of the invention described herein.

Materials and Methods of the Examples

Cells, Viruses, Bacteria

Human embryonic kidney cells 293A (Invitrogen, Carlsbad, California, USA), which is a subclone of the 293 cell line[22] selected for efficiency to generate rAds, human lung adenocarcinoma cell line A549 (ATCC CCL-185), the HAdV-C5 transformed human embryonic retinoblast cell line 911[23] (kindly provided by Urs Greber, Zurich University), and the Cas9 expressing A549-Cas9 cell line[24] were cultured in Dulbecco's modified Eagle medium (DMEM) supplemented with fetal calf serum (FCS 10% v/v, Sigma-Aldrich, St. Louis, Missouri, USA) and penicillin-streptomycin (100 U/ml, Gibco, Carlsbad, California, USA). Additionally, for A549-Cas9 the medium was supplemented with 1 μg/ml Blasticidin (InvivoGen, San Diego, California, USA).

To generate a 293A based cell line with stable expression of codon-optimized SpCas9 (293A-Cas9-B2), we co-transfected low passage 293A cells with Ndel linearized pSG5-Cas9 (described below) and Pvul treated pGC-neo[25] by electroporation using the 25.5 ms square wave protocol at 310 V and infinite resistance, 2 days post transfection the cells were selected by administrating 500 μg/ml G418 (Formedium, Norfolk, United Kingdom). Single clones were picked and analyzed by flow cytometry for Cas9 expression and tested for their permissivity for rAd rescue by co-transfecting pBWH-C5-mChe and pAR-gRNA-Ex (see below). One of the clones (B2), which performed well in both assays, was selected, expanded, and used as adenovirus E1 complementing, Cas9-expressing cell line in this study.

Human Adenovirus B type 3 (HAdV-B3) (prototype strain GB, ATCC VR-847, kindly provided by Thomas Adrian, Hannover Medical School), Human Adenovirus E type 4

(HAdV-E4) (prototype strain RI-67, VR-1572), and the Simian Adenovirus type 25 (SAdV-25, VR-594) were obtained from ATCC. An E1 and E3-deleted human Adenovirus C type 5 vector (Ad5-CMV/mCherry) based rAd vector expressing the reporter mCherry under the hCMViel promoter was obtained from Sirion Biotech (Planegg, Germany). Viral DNA for generation of primary constructs of HAdV-B3 and -E4 as well as for the rAd vector for Ad5-CMV/mCherry was harvested from infected cells as described earlier[26].

The *E. coli* strain NEB10beta (genotype: Δ (ara-leu) 7697 araD139 fhuA ΔlacX74 galK16 galE15 e14-ϕ80dlacZΔM15 recA1 relA1 endA1 nupG rpsL ($Str^R$) rph spoT1 Δ(mrr-hsdRMS-mcrBC)) and NEB5alpha (genotype: fhuA2 Δ(argF-IacZ)U169 phoA gInV44 ϕ80 Δ(lacZ)M15 gyrA96 recA1 relA1 endA1 thi-1 hsdR17) were purchased from New England Biolabs, Frankfurt, Germany. The strain harboring ori6Kγ plasmids Pir-1 (genotype: F-Δlac169 rpoS (Am) robA1 creC510 hsdR514 endA recA1 uidA(ΔMIul)::pir-116) was purchased from Invitrogen (Carlsbad, California, USA).

Plasmids

The oligonucleotides and synthetic DNA fragments used for plasmid constructs or BAC engineering are listed in Table 1. The basic features of the plasmids and rAd constructs generated in this study including their accession numbers are summarized in Tables 2 and 3, respectively.

pO6-A5-mChe-WH was constructed to bring the sgRNA-target site right next to the left ITR of the Ad5 vectors by introducing the Wh-sequence and the mCherry ORF from pmCherry-C1 (Takara, Kusatsu, Japan) into pO6-A5-CMV-gfp (Sirion Biotech, Planegg, Germany). Similarly, pO6-A5-WH18/19-mChe was constructed by inserting the same warhead (Wh) sequence into pO6-A5-CMV, but with a 12 base pair spacer (CAAATTCCTTGG (SEQ ID NO. 58) between the Wh sequence and the ITR. The expression cassette DDD-Cas9 was constructed on the basis of pDD-Cas9 (Addgene Plasmid #90086, kind gift from Sordella Rafella[27]) by inserting a glutamine codon instead of the first methionine codon of the Cas9 coding sequence and the Cas9(wt) cassette was constructed also on the basis of pDD-Cas9 by deleting the DD domain. The sgRNA expression cassette was synthetized by fusing the U6-promoter (GenBank accession no. JN255693.1), to the sgRNA scaffold containing a gRNA targeting-site with low off-target activity described by Yuen et al. 2017[28] (gBlock from IDT, Coralville, Iowa, USA). This sgRNA construct was termed sgRNA-Ex. pHg-RNA-DDD-iGFP, and pH-gRNA-Cas9 (wt)-iGFP were constructed by inserting sgRNA-Ex and the wild type and above described versions of the codon optimized SpCas9[27] expression cassette into vector pH-iGFP (GeneBank Acc 2324217). These constructs were used to insert the CRISPR/Cas-components into the rAd genome containing BACs at their rox site (see below). pSG5-Cas9, used to generate stably Cas9 expressing cell lines, was constructed by inserting the Cas9 ORF from pH-gRNA-Cas9(wt)-Flag into the pSG5 expression vector (Agilent, Santa Clara, California, USA). The high copy plasmid pAR-gRNA-Cas9-Amp coding for the sgRNA-Ex and the Cas9(wt) expression cassette from pH-gRNA-Cas9-Flag was constructed by inserting the respective CRISPR/Cas-components into the PCR amplified vector backbone of pcDNA3.1. The pAR-gRNA-Ex coding for the sgRNA-Ex alone was constructed by amplifying the respective part from pAR-gRNA-Cas9-Amp by PCR and re-ligation of the EcoRI digested amplicon. The pAR-gRNA-IntC5 coding for the exactly cleaving sgRNAs specific for HAdV-5 ITRs (Int5) was constructed by replacing the external targeting sequence of pAR-gRNA-Ex with the corresponding internal targeting sequences (TATATTATTAGATAGCCTC (SEQ ID NO: 59). The pAR-gRNA-Int4 coding for exactly cleaving sgRNAs specific for HAdV-4 and Cas9 was constructed by replacing the external targeting sequence of pAR-gRNA-Cas9-Amp with the corresponding internal targeting sequences for Int4 (TATATTATATAGATAGCCTC (SEQ ID NO: 60).

The plasmid pAR-19, which was used as a bacterial vector backbone to clone viral genomes into high copy plasmids in *E. coli*, was constructed by inserting the above described sgRNA-Ex sequence, the chloramphenicol resistance gene from pKSB2[29] and a rox site into Litmus28 (New England Biolabs, Frankfurt, Germany) replacing its ampicillin resistance gene and MCS.

Plasmids and BACs Encoding for Recombinant Adenoviruses Based on Already Published Ad Constructs The bacterial rAd constructs were generated either by modifying existing rAd constructs to make them compatible to the new rescue technique by introducing CRISPR-Cas target sites (warhead) adjacent to their ITRs (described in this chapter) or by de novo cloning of adenovirus genomes, using Gibson assembly into PCR amplified high copy vectors or BAC-vector fragments (described in the next chapter). To modify genomic constructs we used either recombineering or single step site-specific recombination 3SR[30]. For recombineering we used the methodologies based on either the helper plasmids pKD46[31] or pSC101-BAD-gab-tet (GeneBridges, Berlin, Germany) depending on the selection marker to be applied.

Figures 5A, 5B:
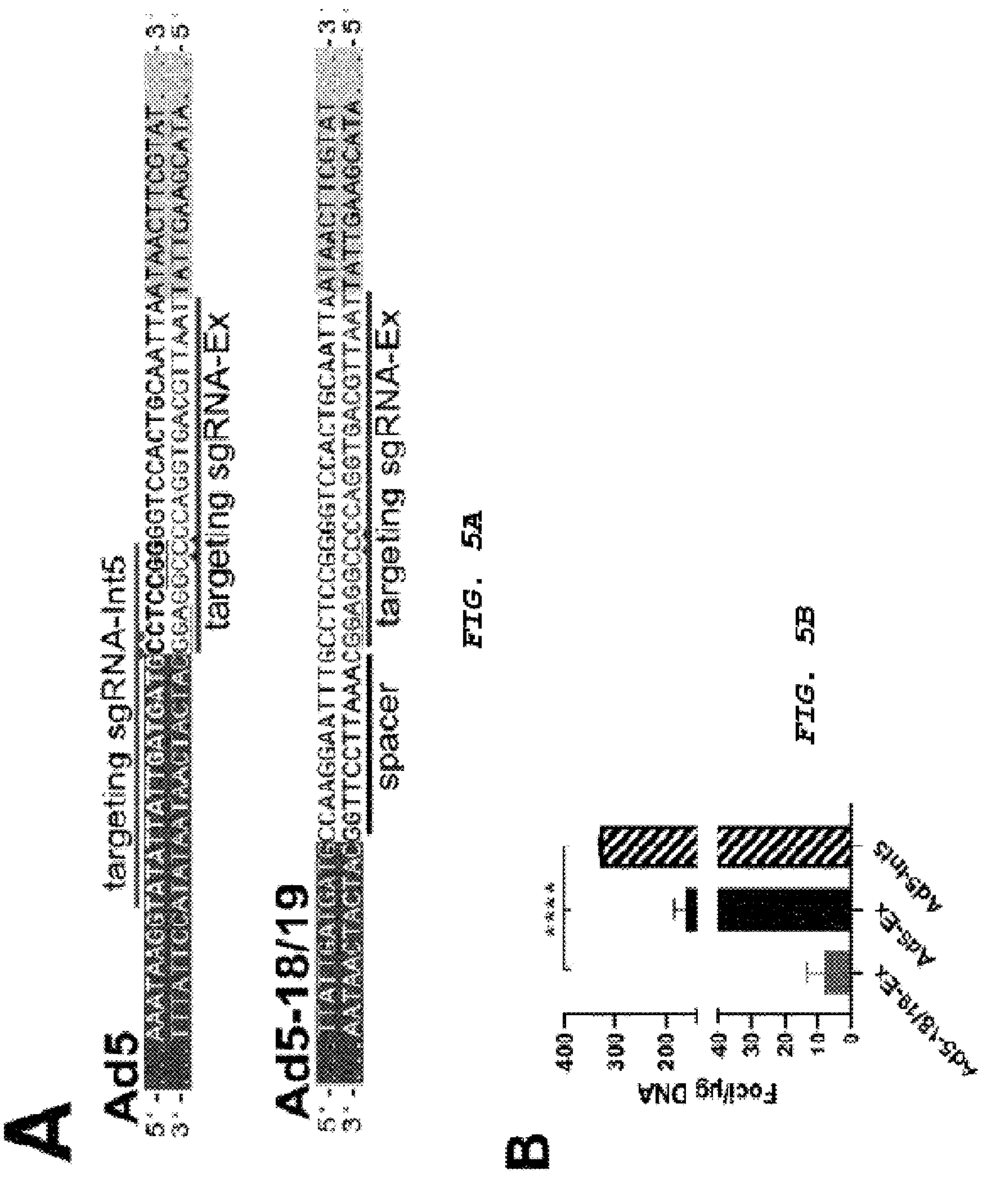
FIG. 5A-D: Impact of exact cleavage on rescue efficiency of recombinant HAdV-5 and HAdV-4.

To tailor existing rAd BACs to the CRISPR/Cas-mediated in vivo terminal resolution we had to introduce sgRNA recognition sites (warheads) adjacent to the Ad genome termini. The resulting construct was termed pBWH-C5-mChe, representing a HAdV-C5 based first generation vector (ΔE1, ΔE3) that was constructed in two steps. First, we inserted pO6-A5-mChe-WH into pBA5-FRT[3] by Flp mediated single step site-specific recombination (Flp-3SR)[30]. This insertion delivered the warhead sequence adjacent to the left ITR and a mCherry expression cassette. This construct was named pBWH-L-C5-mChe. To bring in the second warhead sequence adjacent to the right ITR we performed a two-step recombineering[31], which at the same time allowed i) introduction of a loxP site between the right ITR and the E4 promoter for later insertion of a second transcription unit to this vector as described by Suzuki et al.[32], and ii) insertion of a rox site[33] into the BAC-vector region flanking the right ITR for Dre-mediated 3SR (Dre-3SR)[30]. Similarly, we constructed the pBWH18/19-C5-mChe in two steps: first modifying the right ITR by recombineering with a synthetic linear DNA fragment containing the additional spacer sequences as shown in FIG. 5A and then inserting pO6-A5-WH18/19-mChe into pBA5-FRT-WH18/19 by 3SR. We also modified the same way pBA5-FRT resulting a construct, which is only flanked by warhead sequences at its right ITR (pBWH-R-mChe). The construct pBWH-C5-gRNA-mChe, carrying the expression cassette for the sgRNA-Ex in the bacterial vector backbone was constructed by inserting pH-gRNA into pBWH-C5-mChe by using the Dre-3SR. pBWH-C5-Cas9 carrying the expression cassette only for the Cas9 nuclease in the bacterial vector backbone was constructed by inserting pH-gRNA-Cas9(wt)-iGFP by Dre-3SR into pBWH-C5-mChe.

The construct pBAd5-FG40-GFP resembles the pFG40 construct published earlier[10]. It was constructed by inserting a modified version of pO6-A5-CMV-gfp (Sirion Biotech, Planegg, Germany) into pBA5-FRT. This donor plasmid carried instead of the wild type IRT the palindromic ITR sequences from pFG40 thereby reproducing the pFG40 Ad genome endings in pBA5-FRT background.

A ΔE1ΔE3 first generation vector, BAd19ΔE1ΔE3-GFP, which was constructed on the basis of the ME strain of HAdV-D64 (formerly coined Ad19a)[26] was also tailored for in vivo terminal resolution in two steps. First, the right ITR was flanked by a warhead sequence marked with ampicillin resistance and, then, the left ITR was flanked by the second copy of the warhead sequence marked with Kn resistance by means of recombineering using the respective PCR fragments amplified by primers pairs 64REfor/64RErev and 64LEfor/64LErev resulting in pBWH-D64M-GFP.

De Novo Constructed rAd Genomes for CRISPR/Cas Mediated Terminal Resolution (CTR)

To newly construct bacterial plasmids or BACs capable of CRISPR/Cas mediated terminal resolution we assembled purified genomic Ad DNA with PCR amplified bacterial vector sequences using Gibson assembly[34]. The general workflow used in this study for the de novo construction of rAds is depicted in FIG. 3.

To newly generate rAds, that can be rescued by CRISPR/Cas-mediated terminal resolution we constructed a rAd-plasmid (coined as pAC05-CE1) from a species C derived first generation rAd vector preparation. Genomic rAd DNA was isolated from Ad5-CMV/mChe (Sirion Biotech, Planegg, Germany) infected 293A cells as described above. The genomic Ad DNA was assembled using the NEBuilder reagents according to the manufactory's instruction (New England Biolabs, Frankfurt, Germany) with a PCR amplified vector fragment generated by PCR on a pAR-19 template. The PCR was carried out with primers (LWHC5 for/GHLrev and LWHC5rev/GHLfor) flanked with warhead sequences and with 40 bp homologies to the left and the right ITRs, respectively. The resulting construct are able to also express a sgRNA-Ex and carry a rox site mfor Dre-recombination adjacent to the right ITR. NEB10beta cells were electro-transformed by the assembly mixtures and selected on chloramphenicol plates. Single colonies were picked analyzed by RFLP and selected clones were verified by next generation sequencing.

pAC05-mChe-Cas9 was constructed by inserting the plasmid pH-gRNA-Cas9-Flag into pAC05-CE1 using Dre-3SR.

Figures 5C, 5D:
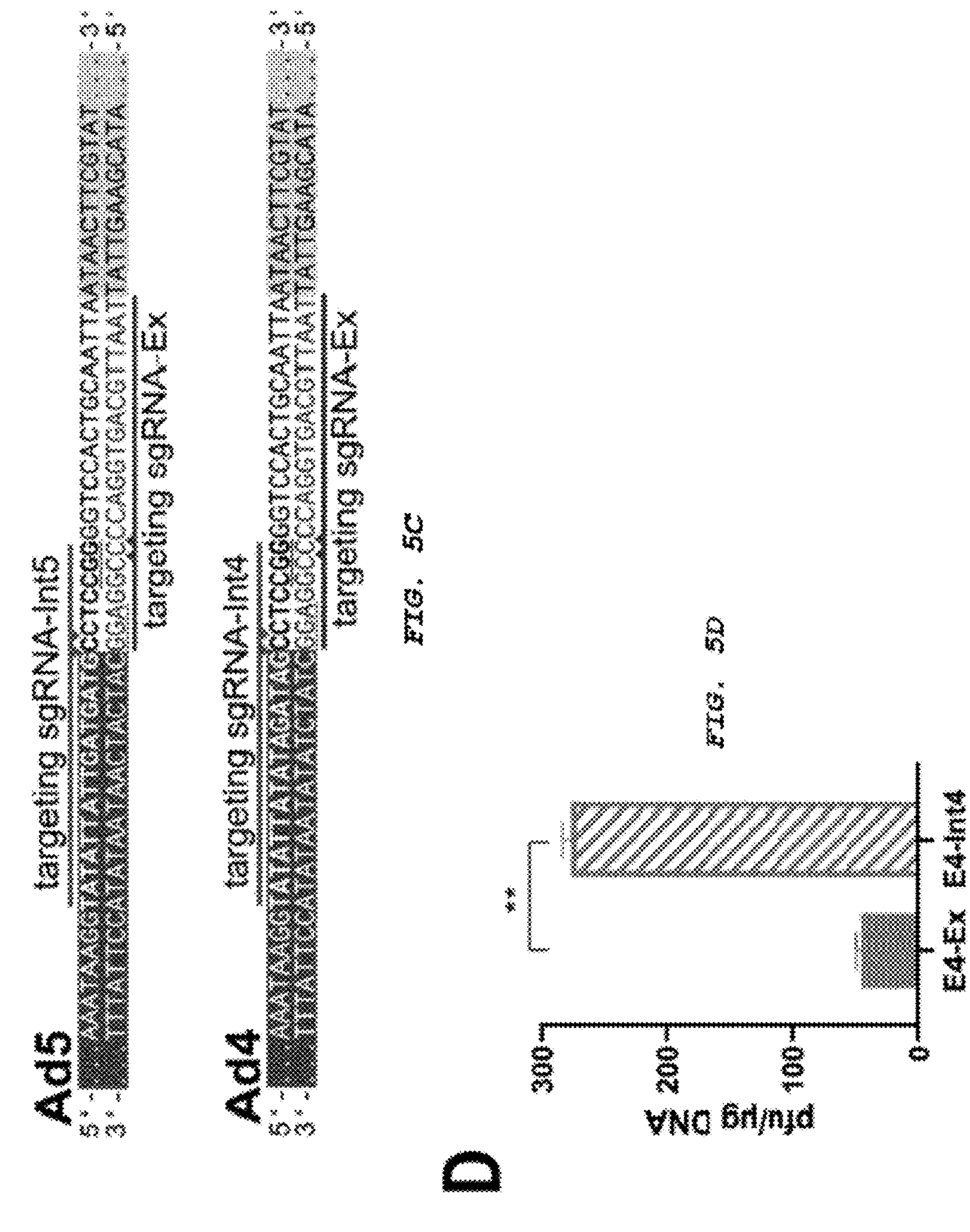

Cloning recombinant HAdV-B3 and HAdV-E4 in *E. coli* followed in principle the same protocol as above. Vector fragments used for Gibson assembly were generated using overlap extension PCRs prepared with Litmus28 (NEB, Frankfurt, Germany) in the case of HAdV-B3 (primers GHLrev/LWHBfor; GHLfor/LWHBrev) and with pKSB2[29] in the case of HAdV-E4 (Primers GHBrev/BWHE4for; GHBfor/BWHE4rev), respectively. In these cases, the final constructs are not equipped to express the sgRNAs. The constructs were assembled using the NEBuilder reagents according to the manufactory's instruction. 2 μl of this finished assembly mix were then electro-transformed into competent *E. coli*. Transformants were selected on Amp and Cam+ plates for the B3 and E4 clones, respectively. Single colonies were picked and analyzed by RFLP and selected clones were verified by next generation sequencing. The verified molecular clones were coined as pLWH-B3 and pBWH-E4, respectively. Since the HAdV-5 based constructs used in this study all carry E3 deletions to obtain comparable genome sizes for the rescue experiments, we deleted the E3 region between nt 27.002 and nt 31.348 (according to the reference sequence GenBank accession no. AY594253) by recombineering. This construct was coined as pBWH-E4-DE3 and was used in this study in the quantitative rescue experiments (FIG. 5D).

Also, a recombinant simian Ad-BACmid (coined as pBWH-SE25) was constructed from genomic DNA of a simian species E adenovirus, isolated from infected cells as described above. The genomic Ad DNA was assembled using the NEBuilder reagents according to the manufactory's instruction (New England Biolabs, Frankfurt, Germany) with two PCR amplified vector fragments generated by PCR on a pKSB2 template. The PCR was carried out with primers (GHBrev/BWHES25for and GHBfor and BWHES25rev) flanked with warhead sequences and with 40 bp homologies to the left and the right ITRs, respectively. NEB10beta cells were electro-transformed by the assembly mixtures and selected on chloramphenicol plates. Single colonies were picked analyzed by RFLP and selected clones were verified by next generation sequencing and coined as pBWH-SE25.

Rescue of rAds by Terminal Resolution

The DNA to be transfected was isolated from bacteria by column purification using the NucleoBond Xtra-Midi-Kit (Macherey Nagel, Oensingen, Switzerland) following the manufacturer's instruction and used directly for transfection of circular constructs. If linearized DNA was transfected, 5 μg column purified DNA was digested overnight in a 100 μl reaction volume using 30 units of the endonuclease Pac (New England Biolabs, Frankfurt, Germany). DNA was then precipitated by adding sodium acetate to a final concentration of 0.3 M and 3 vol. absolute ethanol (Honeywell, Charlotte, North Carolina, USA) and precipitated on ice for 1 hour. Afterwards the DNA precipitates were collected by centrifugation and washed with ethanol (70%) twice. The pellet was dried and re-suspended in 40 μl sterile H2O.

Transfection of 293A, A549, A549-Cas9 or 293-Cas9 cells was performed using Lipofectamine 3000 (ThermoFischer Scientific, Waltham, Massachusetts, USA) according to the instructions of the manufacturer. Using 6 μl Lipofectamine and 5 μl P3000 for transfection mixtures, containing 1 μg rAd plasmid and (if needed) 500 ng (molar ratio, 1:3) helper plasmid DNA, applied on one million cells, seeded 24 h prior to transfection.

The transfection mixtures were added directly into the cell culture media and the cells were incubated overnight. Then, the transfected cells were collected by trypsinization, and ~$1.25\times10^5$ viable cells were seeded into at least 4 wells of a 24-well plate. The cells were observed daily for focus/plaque formation and the foci/plaques were counted one day after the first foci/plaques appeared. In case of lacking plaque formation, cultures were observed for 14 days and then concluded to be negative. The final foci/plaque-counts were normalized to 1 μg DNA.

Next Generation Sequencing

For next generation sequencing (NGS), plasmids or BAC DNA were isolated from *E. coli* by the Xtra-Midi-kit from Macherey Nagel (Duren, Germany), DNA from infected cells was isolated by applying the tissue culture kit (Macherey Nagel, Duren, Germany) according to the manufacturer instructions. The sequencing was done by the Eurofins NSG service using the Illumina MiSeq platform (1.5 GB package) and analyzed by Geneious Prime software following its reference sequence mediated workflow.

Results of the Examples

Fitting Recombinant Adenovirus Genomes to CRISPR-Cas9-Mediated Terminal Resolution rAd genomes normally are released from their circular recombinant form by restriction endonuclease treatment before permissive cells are transfected to rescue recombinant virus (FIG. 1A). The Ad rescue approach described in the present examples is based on targeting the Cas9 nuclease activity to sequences adjacent to the ITRs of the plasmid- or BAC-cloned Ad genomes in order to release the genome termini in vivo (terminal resolution) upon transfection (FIG. 1B), allowing adenovirus DNA replication. Thus, the target sequences for the CRISPR/Cas-complex should be located in close proximity of both ITRs or partially overlap with the ITRs in a way that the actual Cas9-mediated cleavage should occur near or at the ends of the cloned Ad genome (FIG. 1C). To test this principle, we modified an Ad5 (species C) vector, which is the most frequently used recombinant Ad platform. We inserted an artificial CRISPR/Cas target sequence, termed warhead (5'-TAATTGCAGTGGACCCCGG-3' (SEQ ID NO. 30)); together with the required PAM (5'-CGG-3') at each ITR of the BAC-cloned first generation Ad5 vector genome in two steps. First, the reverse complement warhead sequence was inserted directly downstream to the right ITR of the pBAd5-FRT[3] (FIG. 1B). Second, we introduced the warhead sequence directly upstream to the left ITR of the rAd5 donor vector by Flp mediated insertion[30] of an accordingly modified shuttle vector carrying a CMV promoter driven mCherry reporter gene. The position of the PAMs allowed us to either direct the Cas9 with a target sequence complementing the warhead sequence outside of the ITR (Ex) or partially overlapping with the ITR (In) (see FIG. 1C). For the expression of the Cas9 nuclease and the appropriate sgRNA we constructed a separate expression plasmid carrying the two desired transcription units (pAR-gRNA-Cas9-Amp). We also processed two control constructs; one (pBAd5-mChe) contained (a first generation rAd5 genome rescued according to the standard methodology[35]); the other control, pBAd5-FG40-GFP, contained also a first generation rAd5 genome, but instead of its normal ITRs, it possessed the ITR fusion described by Graham et al[10] that was shown to reconstitute the virus after circular DNA transfection as efficiently as the usual method by in vitro linearization.

Rescue of First Generation rAd Vector by CRISPR/Cas9 Mediated In Vivo Terminal Resolution.

Upon co-transfection of pBWH-C5-mChe and pAR-gRNA-Cas9-Amp, as well as upon transfection of the linearized standard construct or the ITR fused control vector into 293A cells, we could observe plaque-formation. However, the CRISPR-Cas driven rescue yielded a much higher number of plaques (see FIG. 2B), and the foci could be observed significantly earlier, already 3-4 days post transfection, compared to either the linear rescue or ITR-fusion driven circular rescue, which yielded foci around 9 to 11 days after transfection. In our hands, the rescue of the ITR-fusion construct showed a slightly higher efficiency although the efficiency was reported to be equal compared reconstitution by enzymatic linearization[10]. Whenever circular pBWH-C5-mChe was transfected alone into 293A, it did not yield infectious particles within the observation period (14 days), indicating that the rescue of Ad5-Warheads-mChe vector requires the presence of a functional CRISPR-Cas system (see FIG. 2 B).

Next, we wanted to investigate whether the CRISPR/Cas mediated vector rescue functions also in the context of a recombinant Ad genome derived from another species of Ads. Thus, we modified a recombinant HAdV-D64 vector[26] to carry the same warhead sequences flanking its ITR, as described above for Ad5 (see FIG. 1 C). Please note, that due to the design, the warhead sequences outside of the ITRs (Ex orientation) can target the Cas9 nuclease to cut the ITRs by a universal gRNA irrespective of the actual ITR sequence and the type of the rAd genome to be rescued. After co-transfection of 293A cells with the warhead-modified species D BAC pBWH-D64-GFP and pAR-gRNA-Cas9-Amp we observed viral plaque formation first at seven days post-transfection while the plaque formation took about fourteen days after transfection of the Pad linearized version of the 64-BAC[26]. In addition, the efficiency of vector rescue after CRISPR/Cas-mediated terminal resolution was again significantly increased (see FIG. 2 C) compared to the rescue of linearized construct.

Figures 2A, 2B, 2C, 2D, 2E:
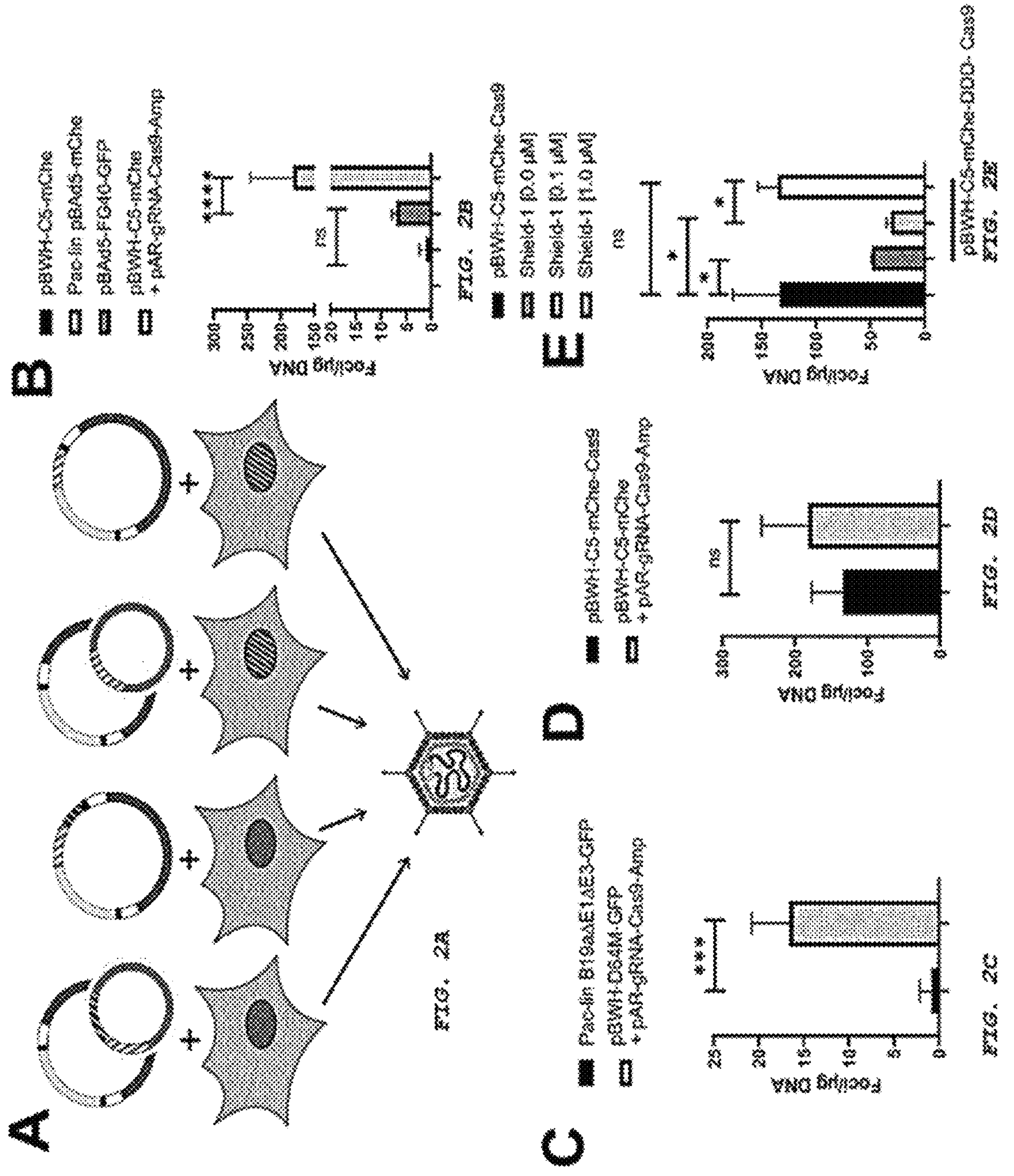
FIG. 2A-H: The main approaches and their efficiency applying CRISPR/Cas9-mediated terminal resolution for adenovirus reconstitution (CTR).

To test the most efficient way to provide the CRISPR/Cas helper function, we first merged all components into a single construct to avoid uncertainties of co-transfection. Therefore, we constructed a mCherry expressing rAd5 BAC that carries the two helper transcription units in addition to a warhead tailored vector genome (pBWH-C5-mChe-Cas9). rAd5 was rescued from this construct as efficiently as from the two-plasmid setting (FIG. 2D).

Next, we wanted to determine whether the activity of Cas9 is required for the in vivo terminal resolution. Therefore, we modified the Cas9 expression unit by replacing the ORF of the wt enzyme with a DD domain regulated Cas9 coding sequence[27]. The DD domain modified Cas9 is instable and therefore less active than the wt Cas9 upon transfection. However, it can be stabilized and functionally rescued by addition of Shield-1, a small molecular stabilizer[36]. We transfected 293A cells with the DDD-Cas9 expressing construct in the absence and presence of Shield-1. As expected, the rescue efficiency after transfection of the circular constructs was drastically reduced in the presence of the destabilized nuclease, and this loss of function was almost fully prevented by addition of Shield-1. This data showed that the rAd rescue by warhead mediated terminal resolution was indeed dependent on Cas9 activity.

Figures 2F, 2G, 2H:
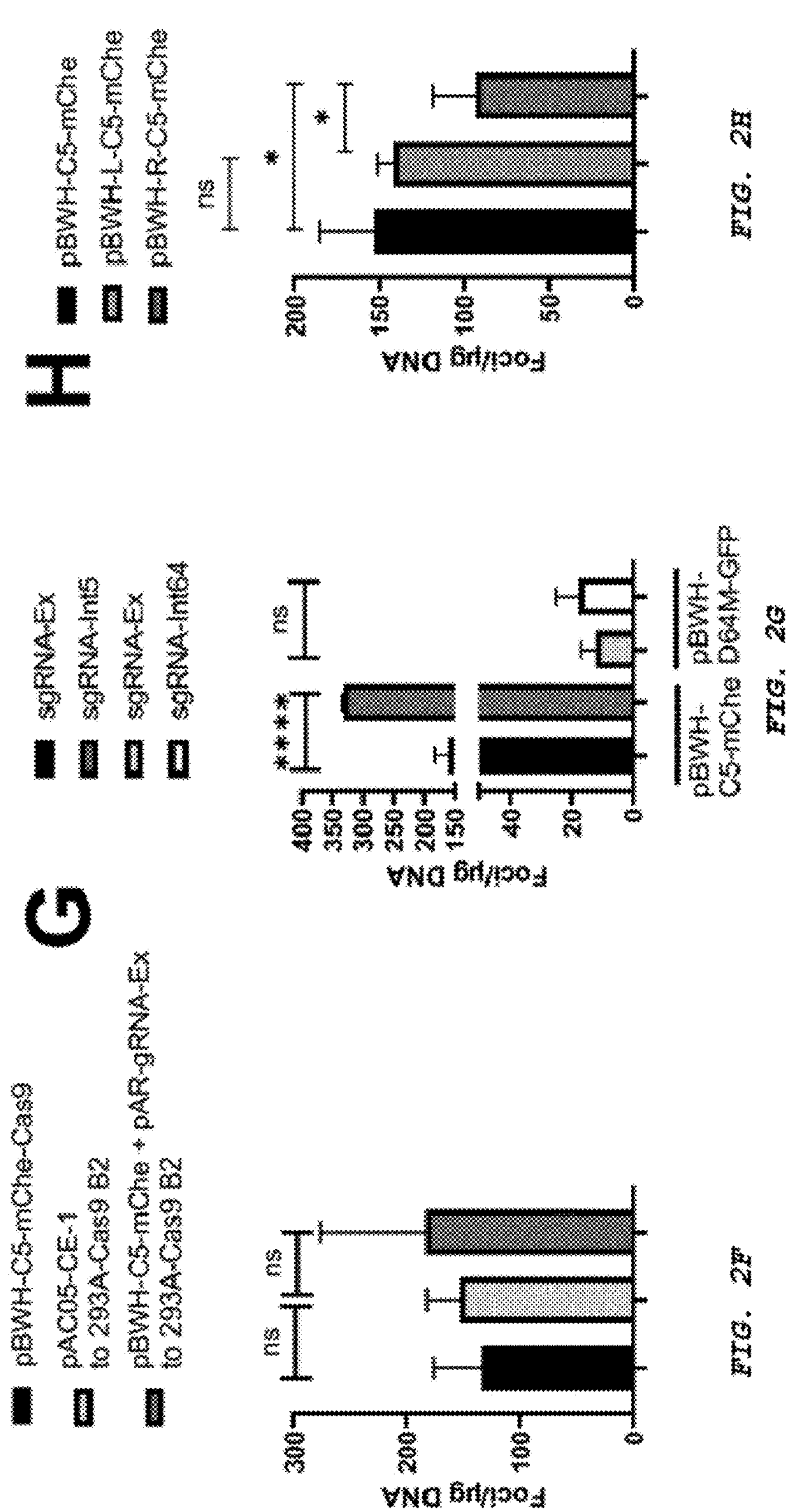

Putting all components in one construct increases the size of the recombinant DNA substantially, which was not a problem, since we used BAC-cloned genomes for these tests. However, BAC constructs are not optimal for high efficiency applications since DNA quality of a high copy plasmid preparation is superior to the quality of BAC preparations. Therefore, to limit the size of the all-in-one construct we generated a cell line based on 293A cells that stably express Flag-tagged SpCas9 under the control of SV40 early-promoter. 19 of the Cas9 positive clones were tested for their ability to mediate vector rescue upon co-transfection of pBWH-C5-mChe and pAR-gRNA-Ex, a construct which expresses the sgRNA-Ex, and selected the clone 293A-Cas9-B2 for further studies since it was able to support terminal resolution and, in addition, expressed the highest level of Cas9 (see FIG. 4). Having the Cas9 expressing complementing cell line in hand allowed us to test the efficiency of high copy plasmid based warheaded rAd constructs, we transfected 293A-Cas9-B2 cells with the pAC05-CE1. As controls we co-transfected either 293A-Cas9-B2 with the basic Ad5 BAC construct pBWH-C5-mChe and pAR-gRNA-Ex, or 293A cells with pBWH-C5-Cas9 carries all necessary components for the in vivo terminal resolution in one construct. We observed plaque formation with the same kinetics and efficiency in all three settings (FIG. 2F). We therefore concluded that the CRISPR/Cas9-component can be provided for in vivo terminal resolution either from the target cell line or by (co-)transfected plasmids without affecting the rescue efficiency. Inserting a functional target sequence of Cas9 nuclease complex outward of the ITRs allowed us to use an universal gRNA for the rescue experiments across various constructs rescuing rAds even based on genomes derived from different adenovirus species. However, based on this design the nature of Cas9 cleavage allows DNA linearization only at relatively distant sites (6-7 base pairs) from the genome ends. While this may not be optimal it is clearly sufficient to induce terminal resolution, as shown above. To induce cleavage closer to or even exactly at the genome ends, we designed another sgRNA (sgRNA-Int) which targets the Cas9 activity to the end of the ITRs and get its PAM from the warhead sequence (see FIG. 1C). To evaluate the efficiency of the closer cut, we co-transfected 293A cells with pBWH-C5-mChe together with pSG5-Cas9 and pAR-gRNA-Ex or pAR-gRNA-IntC5 (5'-CTCCGTAGTAGTTATTATAT-3' (SEQ ID NO. 31)), respectively. In comparison the pAR-gRNA-IntC5 induced almost three times more foci than pAR-gRNA-Ex at the same time (FIG. 2G), indicating that a cleavage closer to the ITR is indeed more efficient than a distant one. However, the design that cut closer to the Ad genome ends requires specific gRNAs, targeting ITRs with different sequences, which may be processed also with different (e.g. unpredictable) efficiency. Therefore, we tested rescue of pBWH-D64-GFP using either pAR-gRNA-Ex or pAR-gRNA-IntD64 (5'-ATTATTAGATAGTTAATTA-3' (SEQ ID NO. 32)). As depicted in FIG. 2G, the yield of the rAds rescued by the Int-construct was also increased, but this did not reach statistical significance for the rescue of the species D genome. These data indicated that the closer the Cas9-nuclease site the better the efficiency of the virus rescue, but the extent of this effect most likely depends on the actual target sequence, and thus needs to be tested for each new construct.

As shown in FIG. 2G, the sgRNA-IntC5 based CTR yielded more than twice as many foci for the HAdV-C5 based construct than the CTR with sgRNA-Ex, indicating that a proximal cleavage induced more efficient rescue than a distant one. To further confirm our conclusion that the distance of the cleavage site from the genome ends matters, we also analyzed the effect of an even more distant cleavage site on CTR. We constructed a new rAd5 based construct, pBWH18/19-C5-mChe, which carried the Wh 12 base pairs further away from the ITR ends (see FIG. 5A lower panel). On this construct, the sgRNA-Ex should induce the Cas9-cleavage 18/19 nucleotide away from the ITR ends. Testing the rescue efficiency of this setting revealed a drastically lower recombinant virus rescue compared to both other settings, which cut closer (FIG. 5B) if it was compared to either the sgRNA-Ex mediated CTR or to the exact cut mediated by sgRNA-Int5 (as in FIG. 2G). These data confirmed that the position of the cleavage site is deterministic for the rescue efficiency of rAd5 based constructs.

To test whether the CRISPR/Cas mediate terminal resolution directed towards only one end of the rAd genome is sufficient for virus rescue, we constructed rAd5 BACmids, which carry the CRISPR/Cas target sequences flanking either the left (pBWH-R-C5-mChe) or the right IRT (pBWH-R-C5-mChe). These constructs along with the original HAdV-5-BACmid pBWH-C5-mChe, which carries the target sequence flanking its both ITRs, were co-transfected with pAR-gRNA-Ex to 293-Cas9 cells. Virus rescue was quantified by determining the primary focus formation as describe above. As depicted in FIG. 2H, transfection of circular DNA of both single ITR labelled construct yielded virus rescue. However, the efficiency of the virus rescue was reduced compared to the double labelled original construct. This drop of recue efficiency was visible for both version but appeared statistically significant only for the construct carry the CRISPR/Cas target flanking the right ITR.

New Construction Pipeline for rAds with CRISPR-Cas-Mediated Terminal Resolution

As shown above, we could modify already cloned rAd genomes in order to make them compatible to CRISPR/Cas-mediated terminal resolution. However, we also wanted to test whether direct construction of recombinant Ads based on CRISPR/Cas-mediated rescue is feasible. This may not be trivial because the introduction of the very same CRISPR/Cas target sequences enlarges the size of inverted repeats which flank the genomes. Thus, we designed a workflow for recombinatorial construction of rAd plasmids and BACs using ITRs extended with the warhead sequences. To test this approach, we associated the wild type HAdV-B3 and HAdV-E4 genomes with a high copy plasmid and a BAC vector, respectively, using Gibson assembly (see FIG. 3 and the material and methods section for detail). This approach resulted in bacterial constructs carrying warhead-flanked infectious rAd genomes (coined as pLWH-B03, for the HAdV-B03 encoding plasmid, and pBWH-E04 for the HAdV-E04 encoding bacmid). Upon co-transfecting of either pBWH-E04 or pLWH-B03 with pAR-gRNA-Ex into A549-Cas9[24] we obtained rescue of infectious viruses with plaque-formation within 4-6 days after transfection. The rescued viruses were propagated and the sequences of both rescued molecular clones of wt rAds (one for B3 and one for E4) were verified by next generation sequencing and compared to the original genomes prepared from the respective starting virus stocks. This data indicates that the enlargement of the ITR with the warhead sequences did not affect recombinatorial cloning of rAd genomes and that the in vivo terminal resolution can function in different cell lines.

The same way we also constructed a BACmid carrying the genomic DNA of Simian Adenovirus type 25. We transfected 293-Cas9 cells with purified BAC DNA prepared from two sequence verified clones of pBWH-SE25 together with the helper plasmid pAR-gRNA-Ex as described above. The transfected cultures were observed daily for plaque formation. Both clones rescued viruses as plaque formation was observed 10-12 day after transfection. Both rescue supernatants were propagated and the sequences of both rescued molecular clones of wt SAdV-25 were verified by next generation sequencing and were identical to the original genomes prepared from the respective starting virus stock. These data indicate that the CRISPR/Cas-mediated in vivo terminal resolution is suitable to rescue recombinant adenoviruses derived from animal host species.

To test whether the presence of the gRNA transcription unit carrying a partial homology to the warhead sequences in the vector backbone would influence the efficiency of the rAd-plasmid assembly by our new work flow, we re-cloned the Ad5-mCherry vector genomes isolated from infected cells by Gibson assembly into the PCR amplified pAR19 vector fragment. This resulted in pAC05-CE1. We did not observe any significant differences between the colony-formations after Gibson assembly using the gRNA transcription unit carrying pAR19 vector fragment compared to the colony formation observed in experiments with standard vectors used for cloning species B and E Ads. The comparison of the NGS of the initial viral DNA with the newly rescued Ad5-mChe-WH confirmed that neither the new cloning procedure nor the CRISPR/Cas-mediated virus rescue affected the primary sequence of the rAds.

ITR-Near CRISPR-Cas Mediated Cleavage in Cells Yielded Efficient Rescue of Recombinant Adenoviruses Based on HAdV-4

Since the primary rescue efficiency after CTR was improved compared to traditional rescue methods for rAds based on HAdV-5, we wanted to test the efficiency of the CTR of rAd derived from another adenovirus species quantitatively. To this end, the new rAd-bacmid based on HAdV-4 (species E) (see for the ITR near sequences in FIG. 5C in comparison with rAd5 construct) was constructed and modified, to allow more exact comparison to the HAdV-5 based construct, by the deletion of the E3 region resulting in the bacmid pBWH-E4-DE3. After co-transfection of 293A cells with this bacmid and helper plasmid pAR-gRNA-Cas9-Amp, which expresses sgRNA-Ex and Cas9, we again observed viral plaque formation. To test the effect of the exact cleavage on the HAdV-4 based vector, we constructed a new helper plasmid, which expressed the sgRNA directing the Cas9 nuclease exactly to the ends of the HAdV-4 genome (pAR-gRNA-Int4, see FIG. 5D). Again, as for the HAdV-5 based rescues, the CTR induced by the exact cleavage improved the rescue efficiency drastically indicating that the release of the rAd ends with exact cleavage is improving efficient rescue.

Discussion of the Examples

Recombinant Ads are one of the most frequently used viral gene transfer vehicles for both in vitro and in vivo applications. Generation of replication-competent rAd vectors is well established. However, the vector rescue from rAd plasmids and bacmids is inefficient. To date, this prevented the use of this vector platform in any technology that is based on direct virus rescue upon transfection, such as propagation of helper-independent replication deficient constructs or genomic library applications. Propagation of high capacity helper virus-free rAd vectors by plasmid transfection is possible but the efficiency of this approach is low. It was previously reported that for preparation of a virus stock which is sufficient for an in vivo mouse experiment about 100 large tissue culture dishes needed to be transfected[37]. Thus, to propagate vectors for human gene therapy this approach definitively requires higher efficiency. It is possible that its low efficiency is determined by the same factor(s), which is important for rescuing replication competent vectors that we have used in this study. We found that using in vivo terminal resolution increased the efficiency of rAd reconstitution by 20-30 fold compared to the traditional method using linear DNA. This could be further increased by three-fold by manipulating the cleavage site of Cas9. It would be interesting to test whether this overall 80-100 fold increase of efficiency can be transferred to the newly described plasmid-based propagation of high capacity rAds. Furthermore, we believe that the gain of efficiency by the rAd rescue with the new methodology described here would allow construction of libraries based on rAd vectors with a size comparable to lentivirus libraries. At optimal conditions, our new system yielded about 30 plaques/$cm^2$ of cell culture. This translates to the generation of libraries with $10^4$-$10^5$ individual clones when transfecting large scale cell culture representing 20-30 large cell culture dishes encompassing about $8.7\times10^4$-$1.3\times10^5$ individual rAd clones in total, respectively). This is comparable to the diversity and the propagation conditions for optimized lentivirus library productions[38]. However, there is a considerable difference between the two platforms which relates to the amplification potential of such high content libraries. While the maximal titer for a lentivirus preparation is about $\sim10^9$ particles/ml, rAd titers can reach titres as high as $\sim10^{13}$ particles/ml[39].

Finally, the possibility to rescue infectious rAds directly from plasmid preparations by the methodology described here also paves the way for new approaches based on rescuing viruses in vivo after plasmid delivery. This would allow the design of a new class of vaccines that would propagate virus particles for optimal immunization after DNA delivery to the vaccinees. The direct DNA delivery, as compared to vaccination using recombinant virus particles, is safer, easier to apply and more economical as it would not require cold-chains[40].

To our knowledge, the here presented CTR is the first approach that allows cutting out the rAd genome from its circular form precisely at the ends of the wild type ITRs. Our data showed the relevance of the accurate cleavage to free the ITRs, since the proximal cleavage resulted in significantly higher adenoviral rescue as compared to the more distant ones (FIGS. 2B and 5B). This may explain why the restriction endonuclease-mediated approaches were relatively inefficient, since they always leave extra nucleotides at both ends of the linearized rAd genomes.

The rescue of the species C construct was improved 2-3-fold by the exact cleavage, and the rescue of species E construct was improved more than 6-fold. According to the in-silico activity scoring (J. G. Doench, E. Hartenian, D. B. Graham, Z. Tothova, M. Hegde, I. Smith, M. Sullender, B. L. Ebert, R. J. Xavier and D. E. Root: Rational design of highly active sgRNAs for CRISPR-Cas9-mediated gene inactivation. Nat Biotechnol, 32(12), 1262-7 (2014)) the sgRNA-Ex (activity score 0.715 and 0.808 targeting E4 and C5, respectively) is far more active than either Int5 or Int4 (0.069 and 0.067, respectively), which definitively does not explain the significant increase of the rescue efficiencies induced by the either Int5 or Int4. We think, the fact that weaker exact cleavage sites induce more efficient rescue than the most active cleavage site in a distant position strongly supports that the critical point of the CTR-efficiency is the ability to cleave exactly. The sgRNA-Ex based CTR functioned less efficiently for HAdV-4 rescue than for HAdV-5 rescue, but the exact cleavage induced an increase, which allowed that the HAdV-4 based construct reached almost the level of HAdV-5 indicating again the importance of the exact cleavage reaching high efficiency rAd rescue. This indicates that the negative effect of the masking nucleotides after distant cleavages may be even more problematic in other species (such as the here shown species E) than for the most extensively studied systems based on HAdV-5.

Determination of Preferred Distances Between the ITRs and the Cas9 Cleavage Side Outside the ITR and Further Improvement of Efficiency New bacmids were constructed, which carry rAD genomes flanked with target sequences for Cas9 cleavage, which are located more distantly from the ITRs than described in the examples above (such as about 10-20 base pairs outside the ITRs) to find out how far one can move the Cas9 cut from the external ends of the ITRs. Efficiency of virus rescue upon transfection of these constructs is compared to the rescue efficiency of the construct, which is cut at the closest possible external site in the presence of the co-expression of the appropriate gRNA and Cas9 expression. In particular, efficiency of constructs where Cas9 cuts 0/1, 6/7, 12/13 and 18/19 nucleotides form the ITR are compared. Constructs which are cut even further away from the ITR can also be tested. These experiments provide information about the most distant useful position of Cas9 target sequences for successful rAd rescue.

The activity scores of the sgRNAs Int5 and Int4 are significantly lower that the activity score of the sgRNA Ex. The recue efficiencies upon targeting nt5 and nt4 site are, in contrast much higher. This clearly indicates that the major factor is the distance of the cleavage site determining the CTR efficiency. However, it is not clear that the cleavage efficiency plays a measurable role. We are also testing the effect of the cleavage efficiency measured by the Doench-score on the rescue efficiency by the exact cleavage. By modifying the variable first 8 positions of the ITRs and the 4 nucleotides between the ITRs and the PAM sequences, it is possible to design new genome endings and flanking sequences, which allow to use sgRNAs with 4-6 fold higher Doench-sores than the here represented nt5 and Int4 settings. It will be interesting to see whether how much the improvement of the CRISPR/Cas targeting influences the rescue efficiencies of the different constructs.

Tables of the Examples

TABLE 1

Oligonucleotides of the examples

| Name | Sequence (5'- 3') | Length [bp] | Application | SEQ ID NO. |
|---|---|---|---|---|
| AmpEcoRI | GTGTGAATTCGTCAGGTGGCACT TTTCGGGG | 31 | Cloning pH-gRNA-Cas9 (wt)-iGFP | SEQ ID NO. 1 |
| AmpPacI | GTGTTTAATTAAACTTGGTCTGAC AGTTACC | 31 | Cloning pH-gRNA-Cas9 (wt)-iGFP | SEQ ID NO. 2 |
| AmpXho_for | GTGTCTCGAGTCAGGTGGCACTT TTCG | 27 | Cloning pH-gRNA-Cas9 (wt)-iGFP | SEQ ID NO. 3 |
| PUCNsi_rev | GTGTATGCATCGCAGGAAAGAAC ATGTGAGC | 31 | Cloning pH-gRNA-Cas9 (wt)-iGFP | SEQ ID NO. 4 |
| Cas9for | GTGTACCGGTTCTAGAGCCAC | 21 | Cloning pSG5-Cas9 | SEQ ID NO. 5 |
| Cas9rev | CTGAAGATCTCTTGCAGATAGC | 22 | Cloning pSG5-Cas9 | SEQ ID NO. 6 |
| gRNANsi_for | GTGTATGCATTATCGTTTCAGACC CACCT | 29 | Cloning pH-gRNA-Cas9 (wt)-iGFP | SEQ ID NO. 7 |
| gRNAEcoR_rev | TGTGGAATTCAAGCTTAAAAAAGC ACCGACTC | 32 | Cloning pH-gRNA-Cas9 (wt)-iGFP | SEQ ID NO. 8 |
| Warhead-L-ITR19a_for | GTGTTTAATTAATAATTGCAGTGG ACCCCGGAGGCTATCTAATAATAT ACCCCACAAAG | 59 | Cloning p06-19a-CMV-GFP-Warhead | SEQ ID NO. 9 |
| Warhead-L-ITR19a_rev | TGTGCATATGATACACTTGATGT | 23 | Cloning p06-19a-CMV-GFP-Warhead | SEQ ID NO. 10 |
| GHBfor | CCGCGTGTGTACCTCTACCTGGA GTTTTTCCCACGGTGGA | 40 | Assembly for warheaded HAdE4 into a pKSB2 | SEQ ID NO. 11 |
| GHBrev | TCCACCGTGGGAAAAACTCCAGG TAGAGGTACACACGCGG | 40 | Assembly for warheaded HAdE4 into a pKSB2 | SEQ ID NO. 12 |
| GHLfor | GTCTATCAGGGCGATGGCCCACT ACGTGAACCATCACCCA | 40 | Assembly for warheaded HAdB3 and HAdC5 into pAR19 | SEQ ID NO. 13 |
| GHLrev | TGGGTGATGGTTCACGTAGTGGG CCATCGCCCTGATAGAC | 40 | Assembly for warheaded HAdB3 and HAdC5 into PAR19 | SEQ ID NO. 14 |
| BWHE4for | TTAACTCACACAAAAAAAATAAGG TATATTATATAGATAGCCTCCGGG GTCCACTGCAATTACTTCTCGACC AATTCTCATGTTTGAC | 86 | Assembly for warheaded HAdE4 into a pKSB2 | SEQ ID NO. 15 |
| BWHE4rev | TTAACTCACACAAAAAAAATAAGG TATATTATATAGATAGCCTCCGGG GTCCACTGCAATTATAAACTCGAC AGCGACACACTTGC | 86 | Assembly for warheaded HAdE4 into a pKSB2 | SEQ ID NO. 16 |

TABLE 1-continued

Oligonucleotides of the examples

| Name | Sequence (5'- 3') | Length [bp] | Application | SEQ ID NO. |
|---|---|---|---|---|
| LWHB3for | GTTGGCACCATTCCATCTATAAGG TATATTATATAGATAGCCTCCGGG GTCCACTGCAATTAGGTACCCTCT AGTCAAGGCCTTAA | 86 | Assembly for warheaded HAdB3 into pAR19 | SEQ ID NO. 17 |
| LWHB3rev | GTTGGCACCATTCCATCTATAAGG TATATTATATAGATAGCCTCCGGG GTCCACTGCAATTACGGTGCGCG CGATGCATTCGAAGA | 86 | Assembly for warheaded HAdB3 into pAR19 | SEQ ID NO. 18 |
| LWHC5for | TATTGGCTTCAATCCAAAATAAGG TATATTATTGATGATGCCTCCGGG GTCCACTGCAATTAGGTACCCTCT AGTCAAGGCCTTAA | 86 | Assembly for warheaded HAdC5 into pAR19 | SEQ ID NO. 19 |
| LWHC5rev | TATTGGCTTCAATCCAAAATAAGG TATATTATTGATGATGCCTCCGGG GTCCACTGCAATTACGGTGCGCG CGATGCATTCGAAGA | 86 | Assembly for warheaded HAdC5 into pAR19 | SEQ ID NO. 20 |
| 64LEfor | TGAATGGCAGAAATTCGATGATAA GCTGTCAAACATGAGAATGGGTC GAGAACAGGTTGAACTGCTGATC TTCAG | 75 | Flanking the left ITR of B19aΔE1ΔE3-gfp with warhead seq. | SEQ ID NO. 21 |
| 64LErev | TCATTTGCATATTAACTTTTGTTTA CTTTGTGGGGTATATTATTAGATA GCCTCCGGGGTCCACTGCAATTA TTAATTAAGCCAGTGTTACAACCA ATTAA | 101 | Flanking the left ITR of B19aΔE1ΔE3-gfp with warhead seq | SEQ ID NO. 22 |
| 64REfor | TCATTTGCATATTAACTTTTGTTTA CTTTGTGGGGTATATTATTAGATA GCCTCCGGGGTCCACTGCAATTA TAACTTTAAATAATGCCAA | 91 | Flanking the right ITR of B19aΔE1ΔE3-gfp with warhead seq | SEQ ID NO. 23 |
| 64RErev | ATCCGATGCAAGTGTGTCGCTGT CGAGTTTAAACATGCATCCTTAAT TAAACGCGTTTACCAATGCTTAAT C | 72 | Flanking the right ITR of B19aΔE1ΔE3-gfp with warhead seq | SEQ ID NO. 24 |
| BWHSE25for | TAACGCGCACAAAAAGTTTGAGGT ATATTATTGATGATGGCCTCCGGG GTCCACTGCAATTACTTCTCGACC AATTCTCATGTTTGAC | 88 | Assembly for warheaded SAdV-E25 into a pKSB2 | SEQ ID NO. 25 |
| BWHSE25rev | TAACGCGCACAAAAAGTTTGAGGT ATATTATTGAAGATGGCCTCCGGG GTCCACTGCAATTATAAACTCGAC AGCGACACACTTGC | 86 | Assembly for warheaded SAdV-E25 into a pKSB2 | SEQ ID NO. 26 |

TABLE 2

Synthetic DNA fragments

| Name | Sequence (5'- 3') | Length [bp] | Application | SEQ ID NO. |
|---|---|---|---|---|
| loxE4Amp | TTACCAGTAAAAAAGAAAACCTATTAAAA AAACACCACTCGACACGGCACATAACTTC GTATAGCATACATTATACGAAGTTATCAG CTCAATCAGTCACAGTGTAAAAAAGGGCC AAGTGCAGAGCGAGTATATATAGGACTAA AAAATGACGTAACGGTTAAAGTCCACAAA AAACACCCAGAAAACCGCACGCGAACCTA CGCCCAGAAACGAAAGCCAAAAAACCCAC AACTTCCTCAAATCGTCACTTCCGTTTTC CCACGTTACGTCACTTCCCATTTTAAGAA AACTACAATTCCCAACACATACAAGTTAC TCCGCCCTAAAACCTACGTCACCCGCCCC GTTCCCACGCCCCGCGCCACGTCACAAAC TCCACCCCCTCATTATCATATTGGCTTCA | 1.732 | Construction of pBWH-C5-mChe | SEQ ID NO. 27 |

TABLE 2-continued

| Synthetic DNA fragments | | | | |
|---|---|---|---|---|
| Name | Sequence (5'- 3') | Length [bp] | Application | SEQ ID NO. |
| | ATCCAAAATAAGGTATATTATTGATGATG TTAATTAAGGGCGGCCGCACGGGCCATCG ATGGGGATCCATCCGCGGAGAAGCTTCTC GACCAATTCTCATGTTTGACAGCTTATCA TCGAATTTCTGCCATTCATCCGCTTATTA TCACTTATTCAGGCGTAGCAACCAGGCGT TTAAGGGCACCAATAACTGCCTTAAAAAA AAAATCAATCTAAAGTATATATGAGTAAA CTTGGTCTGACAGTTACCAATGCTTAATC AGTGAGGCACCTATCTCAGCGATCTGTCT ATTTCGTTCATCCATAGTTGCCTGACTCC CCGTCGTGTAGATAACTACGATACGGGAG GGCTTACCATCTGGCCCCAGTGCTGCAAT GATACCGCGAGACCCACGCTCACCGGCTC CAGATTTATCAGCAATAAACCAGCCAGCC GGAAGGGCCGAGCGCAGAAGTGGTCCTGC AACTTTATCCGCCTCCATCCAGTCTATTA ATTGTTGCCGGGAAGCTAGAGTAAGTAGT TCGCCAGTTAATAGTTTGCGCAACGTTGT TGCCATTGCTACAGGCATCGTGGTGTCAC GCTCGTCGTTTGGTATGGCTTCATTCAGC TCCGGTTCCCAACGATCAAGGCGAGTTAC ATGATCCCCCATGTTGTGCAAAAAAGCGG TTAGCTCCTTCGGTCCTCCGATCGTTGTC AGAAGTAAGTTGGCCGCAGTGTTATCACT CATGGTTATGGCAGCACTGCATAATTCTC TTACTGTCATGCCATCCGTAAGATGCTTT TCTGTGACTGGTGAGTACTCAACCAAGTC ATTCTGAGAATAGTGTATGCGGCGACCGA GTTGCTCTTGCCCGGCGTCAACACGGGAT AATACCGCGCCACATAGCAGAACTTTAAA AGTGCTCATCATTGGAGAACGTTCTTCGG GGCGAAAACTCTCAAGGATCTTACCGCTG TTGAGATCCAGTTCGATGTAACCCACTCG TGCACCCAACTGATCTTCAGCATCTTTTA CTTTCACCAGCGTTTCTGGGTGAGCAAAA ACAGGAAGGCAAAATGCCGCAAAAAAGGG AATAAGGGCGACACGGAAATGTTGAATAC TCATACTCTTCCTTTTTCAATATTATTGA AGCATTTATCAGGGTTATTGTCTCATGAG CGGATACATATTTGAATGTATTTAGAAAA ATAAACAAATAGGGGTTCCGCGCACATTT CCCCGAAAAGTGCCACCTGACGTAGTTAA CAAAAAAAAGCCCGCCGAAGCGGGCTTTA TTTAGCTTCCTTAGCTCCTGAAAATCTCG ATAACTCAAAAAATACGCCCG | | | |
| ROXITRCam | TTACCAGTAAAAAAGAAAACCTATTAAAA AAACACCACTCGACACGGCACCAGCTCAA TCAGTCACAGTGTAAAAAAGGGCCAAGTG CAGAGCGAGTATATATAGGACTAAAAAAT GACGTAACGGTTAAAGTCCACAAAAAACA CCCAGAAAACCGCACGCGAACCTACGCCC AGAAACGAAAGCCAAAAAACCCACAACTT CCTCAAATCGTCACTTCCGTTTTCCCACG TTACGTCACTTCCCATTTTAAGAAAACTA CAATTCCCAACACATACAAGTTACTCCGC CCTAAAACCTACGTCACCCGCCCCGTTCC CACGCCCCGCGCCACGTCACAAACTCCAC CCCCTCATTATCATATTGGCTTCAATCCA AAATAAGGTATATTATTGATGATGCCTCC GGGGTCCACTGCAATTAATAACTTCGTAT AGCATACATTATACGAAGTTATTTAATTA AGGGCGGCCGCACGGGCCATCGATGGGGA TCCTAACTTTAAATAATGCCAATTATTTA AAGTTAATCCGCGGAGAAGCTTCTCGACC AATTCTCATGTTTGACAGCTTATCATCGA ATTTCTGCCATTCATCCGCTTATTATCAC TTATTCAGGCGTAGCAACCAGGCGTTTAA GGGCACCAATAACTGCCTTAAAAAAATTA CGCCCCGCCCTGCCACTCATCGCAGTACT GTTGTAATTCATTAAGCATTCTGCCGACA TGGAAGCCATCACAGACGGCATGATGAAC CTGAATCGCCAGCGGCATCAGCACCTTGT CGCCTTGCGTATAATATTTGCCCATGGTG | 1.374 | Construction of pBWH-C5-mChe | SEQ ID NO. 28 |

TABLE 2-continued

| Synthetic DNA fragments | | | | |
|---|---|---|---|---|
| Name | Sequence (5'- 3') | Length [bp] | Application | SEQ ID NO. |
| | AAAACGGGGGCGAAGAAGTTGTCCATATT GGCCACGTTTAAATCAAAACTGGTGAAAC TCACCCAGGGATTGGCTGAGACGAAAAAC ATATTCTCAATAAACCCTTTAGGGAAATA GGCCAGGTTTTCACCGTAACACGCCACAT CTTGCGAATATATGTGTAGAAACTGCCGG AAATCGTCGTGGTATTCACTCCAGAGCGA TGAAAACGTTTCAGTTTGCTCATGGAAAA CGGTGTAACAAGGGTGAACACTATCCCAT ATCACCAGCTCACCGTCTTTCATTGCCAT ACGGAATTCCGGATGAGCATTCATCAGGC GGGCAAGAATGTGAATAAAGGCCGGATAA AACTTGTGCTTATTTTTCTTTACGGTCTT TAAAAAGGCCGTAATATCCAGCTGAACGG TCTGGTTATAGGTACATTGAGCAACTGAC TGAAATGCCTCAAAATGTTCTTTACGATG CCATTGGGATATATCAACGGTGGTATATC CAGTGATTTTTTTCTCCATTTTAGCTTCC TTAGCTCCTGAAAATCTCGATAACTCAAA AAATACGCCCG | | | |
| Waroxamp | TCATTTGCATATTAACTTTTGTTTACTTT GTGGGGTATATTATTAGATAGCCTCCGGG GTCCACTGCAATTATAACTTTAAATAATG CCAATTATTTAAAGTTAATCCGCGGAGAAC GCGTGCCGCGGAACCCCTATTTGTTTATT TTTCTAAATACATTCAAATATGTATCCGC TCATGAGACAATAACCCTGATAAATGCTT CAATAATATTGAAAAAGGAAGAGTATGAG TATTCAACATTTCCGTGTCGCCCTTATTC CCTTTTTTGCGGCATTTTGCCTTCCTGTT TTTGCTCACCCAGAAACGCTGGTGAAAGT AAAAGATGCTGAAGATCAGTTGGGTGCAC GAGTGGGTTACATCGAACTGGATCTCAAC AGCGGTAAGATCCTTGAGAGTTTTCGCCC CGAAGAACGTTTCCCAATGATGAGCACTT TTAAAGTTCTGCTATGTGGCGCGGTATTA TCCCGTGTTGACGCCGGGCAAGAGCAACT CGGTCGCCGCATACACTATTCTCAGAATG ACTTGGTTGAGTACTCACCAGTCACAGAA AAGCATCTTACGGATGGCATGACAGTAAG AGAATTATGCAGTGCTGCCATAACCATGA GTGATAACACTGCGGCCAACTTACTTCTG ACAACGATCGGAGGACCGAAGGAGCTAAC CGCTTTTTTGCACAACATGGGGGATCATG TAACTCGCCTTGATCGTTGGGAACCGGAG CTGAATGAAGCCATACCAAACGACGAGCG TGACACCACGATGCCTGTAGCAATGGCAA CAACGTTGCGCAAACTATTAACTGGCGAA CTACTTACTCTAGCTTCCCGGCAACAATT AATAGACTGGATGGAGGCGGATAAAGTTG CAGGACCACTTCTGCGCTCGGCCCTTCCG GCTGGCTGGTTTATTGCTGATAAATCTGG AGCCGGTGAGCGTGGGTCTCGCGGTATCA TTGCAGCACTGGGGCCAGATGGTAAGCCC TCCCGTATCGTAGTTATCTACACGACGGG GAGTCAGGCAACTATGGATGAACGAAATA GACAGATCGCTGAGATAGGTGCCTCACTG ATTAAGCATTGGTAAACGCGTTTAATTAA GGATGCATGTTTAAACTCGACAGCGACAC ACTTGCATCGGAT | 1.145 | Construction of pBWH-D64-GFP | SEQ ID NO. 29 |

TABLE 3

| Plasmid constructs used in the examples<br>Plasmids | | |
|---|---|---|
| Name | Properties | GenBank |
| pAR19 | Constitutive sgRNA expression under human U6 promoter, targeting warhead sequence; single rox target site; chloramphenicol acetyltransferase (CamR) | |
| pH-gRNA-Cas9-Flag | Constitutive sgRNA expression under human U6 promoter, targeting warhead sequence; single rox target site; Constitutive hu-SpCas9-Flag-NLS under EF1α promoter; expression β-lactamase expression (AmpR); tsmut-repA* | |
| pH-gRNA-Cas9(wt)-iGFP-Flag | Constitutive sgRNA expression under human U6 promoter, targeting warhead sequence; single rox target site; Constitutive hu-SpCas9-Flag-NLS under EF1α promoter; internal ribosomal entry site (IRES) GFP downstream of SpCas9; expression β-lactamase expression (AmpR); tsmut-repA[1] | |
| pAR-gRNA-Ex | Constitutive sgRNA expression under human U6 promoter, targeting warhead sequence; β-lactamase expression (AmpR) | |
| pAR-gRNA-IntC5 | Constitutive sgRNA expression under human U6 promoter, targeting 5' of HAdC5-ITR sequence; β-lactamase expression (AmpR) | |
| pAR-gRNA-IntC64 | Constitutive sgRNA expression under human U6 promoter, targeting 5' of HAdD64-ITR sequence; β-lactamase expression (AmpR) | |
| pAR-gRNA-Cas9-Amp | Constitutive sgRNA expression under human U6 promoter, targeting warhead sequence; Constitutive hu-SpCas9-Flag-NLS under EF1α promoter; β-lactamase expression (AmpR) | |
| pAR-gRNA-Int4-Cas9-Amp | Constitutive sgRNA expression under human U6 promoter, targeting 5' of HAdC4-ITR sequence; Constitutive hu-SpCas9-Flag-NLS under EF1α promoter; β-lactamase expression (AmpR) | |
| pO6-A5-mChe-Warhead | Constitutive mChe expression under hCMV-ie-promoter; upstream of L-ITR (HAdC5) warhead sequence; aminoglycoside phosphotransferase (KanR); ori6Kγ replication origin | |
| pO6-A64-GFP-Warhead | Constitutive GFP expression under hCMV-ie-promoter; upstream of L-ITR (HAdD64) warhead sequence; aminoglycoside phosphotransferase (KanR); ori6Kγ replication origin | |
| PSG5-Cas9 | Expression of hu-SpCas9-Flag-NLS under SV40LT promoter; mRNA codes additionally for beta-globulin intron; β-lactamase expression (AmpR) | |
| pO6-A5-WH18/19-mChe | Constitutive mChe expression under hCMV-ie-promoter; upstream of L-ITR (HAdC5) warhead sequence with 12 basepair spacer; aminoglycoside phosphotransferase (KanR); ori6Kγ replication origin | |

*Hashimoto-Gotoh, T., Franklin, F. C., Nordheim, A. & Timmis, K. N. Specific-purpose plasmid cloning vectors. I. Low copy number, temperature-sensitive, mobilization-defective pSC101-derived containment vectors. *Gene* 16, 227-235, doi: 10.1016/0378-1119(81)90079-2 (1981).

TABLE 4

| Recombinant adenovirus plasmids and BACs. | |
|---|---|
| Name | Properties |
| pBAd5-FG40-GFP | BAC coding for HAdV-C5-ΔE1ΔE3 genome; ITR proximity at E1 locus*; Expression of green fluorescence protein (GFP) under hCMV-ie-promoter; chloramphenicol acetyltransferase expression (CamR); |
| pBWH-C5-mChe | BAC coding for HAdV-C5-ΔE1ΔE3 genome; both ITRs flanked by warhead sequence; Expression of mCherry under hCMV-ie-promoter; chloramphenicol acetyltransferase expression (CamR); aminoglycoside phosphotransferase (KanR); |
| pBWH-L-C5-mChe | BAC coding for HAdV-C5-ΔE1ΔE3 genome; The left ITR is flanked by warhead sequence; Expression of mCherry under hCMV-ie-promoter; chloramphenicol acetyltransferase expression (CamR); aminoglycoside phosphotransferase expression (KanR); |

TABLE 4-continued

Recombinant adenovirus plasmids and BACs.

| Name | Properties |
|---|---|
| pBWH-R-C5-mChe | BAC coding for HAdV-C5-ΔE1ΔE3 genome; ITRs flanked by warhead sequence; Expression of mCherry under hCMV-ie-promoter; chloramphenicol acetyltransferase expression (CamR); |
| pBWH-C5-Cas9 | BAC coding for HAdV-C5-ΔE1ΔE3 genome; ITRs flanked by warhead sequence; Expression of mCherry under hCMV-ie-promoter; Expression of sgRNA-Ex under the U6-promoter; Expression of hSp-Cas9 under EF1α-promoter; chloramphenicol acetyltransferase expression (CamR); aminoglycoside phosphotransferase (KanR); β-lactamase expression (AmpR); |
| pAC05-CE1 | High copy plasmid coding for HAdV-C5-ΔE1ΔE3 genome; ITRs flanked by warhead sequence; Expression of mCherry under hCMV-ie-promoter; Expression of sgRNA-Ex under the U6-promoter; chloramphenicol acetyltransferase expression (CamR); aminoglycoside phosphotransferase (KanR); |
| pAC05-mChe-Cas9 | High copy plasmid coding for HAdV-C5-ΔE1ΔE3 genome; ITRs flanked by warhead sequence; Expression of mCherry under hCMV-ie-promoter; Expression of sgRNA-Ex under the U6-promoter; Expression of hSp-Cas9 under EF1α-promoter; chloramphenicol acetyltransferase expression (CamR); aminoglycoside phosphotransferase (KanR); β-lactamase expression (AmpR); |
| pLWH-B3 | High copy plasmid coding for HAdV-B3 genome; ITRs flanked by warhead sequence; B-lactamase expression (AmpR); |
| pBWH-E4 | BAC coding for HAdV-E4 genome; ITRs flanked by warhead sequence; chloramphenicol acetyltransferase expression (CamR); |
| pBWH-D64M-GFP | BAC coding for HAdV-D64-ΔE1ΔE3 genome; both ITRs flanked by warhead sequence; Expression of GFP under hCMV-ie-promotor; chloramphenicol acetyltransferase expression (CamR); aminoglycoside phosphotransferase (KanR); β-lactamase expression (AmpR); |
| pBWH-E4-DE3 | BAC coding for HAdV-E4 genome with the deletion of E3 region; ITRs flanked by warhead sequence; chloramphenicol acetyltransferase expression (CamR); |
| pBWH18/19-C5-mChe | BAC corresponding to pBWH-C5-mChe with inserted spacer according to FIG. 5A. |

*Graham, F. L. Covalently closed circles of human adenovirus DNA are infectious. *The EMBO journal* 3, 2917-2922 (1984).

REFERENCES

1 Ghosh-Choudhury, G., Haj-Ahmad, Y., Brinkley, P., Rudy, J. & Graham, F. L. Human adenovirus cloning vectors based on infectious bacterial plasmids. *Gene* 50, 161-171, doi: 10.1016/0378-1119 (86) 90321-5 (1986).

2 Chartier, C. et al. Efficient generation of recombinant adenovirus vectors by homologous recombination in *Escherichia coli*. *Journal of virology* 70, 4805-4810 (1996).

3 Ruzsics, Z., Lemnitzer, F. & Thirion, C. Engineering adenovirus genome by bacterial artificial chromosome (BAC) technology. *Methods Mol Biol* 1089, 143-158, doi: 10.1007/978-1-62703-679-5_11 (2014).

4 Smart, J. E. & Stillman, B. W. Adenovirus terminal protein precursor. Partial amino acid sequence and the site of covalent linkage to virus DNA. *J Biol Chem* 257, 13499-13506 (1982).

5 Russell, W. C. Update on adenovirus and its vectors. *The Journal of general virology* 81, 2573-2604, doi: 10.1099/0022-1317-81-11-2573 (2000).

6 Cherng, J. Y. et al. Effect of DNA topology on the transfection efficiency of poly((2-dimethylamino)ethyl methacrylate)-plasmid complexes. *J Control Release* 60, 343-353, doi: 10.1016/s0168-3659 (99) 00089-9 (1999).

7 Chancham, P. & Hughes, J. A. Relationship between plasmid DNA topological forms and in vitro transfection. *J Liposome Res* 11, 139-152, doi: 10.1081/LPR-100108458 (2001).

8 Webster, A., Leith, I. R., Nicholson, J., Hounsell, J. & Hay, R. T. Role of preterminal protein processing in adenovirus replication. *Journal of virology* 71, 6381-6389 (1997).

9 Sharp, P. A., Moore, C. & Haverty, J. L. The infectivity of adenovirus 5 DNA-protein complex. *Virology* 75, 442-456, doi: 10.1016/0042-6822 (76) 90042-8 (1976).

10 Graham, F. L. Covalently closed circles of human adenovirus DNA are infectious. *The EMBO journal* 3, 2917-2922 (1984).

11 Hille, F. & Charpentier, E. CRISPR-Cas: biology, mechanisms and relevance. *Philosophical transactions of the Royal Society of London*. Series B, Biological sciences 371, doi: 10.1098/rstb.2015.0496 (2016).

12 Cong, L. et al. Multiplex genome engineering using CRISPR/Cas systems. *Science* 339, 819-823, doi: 10.1126/science.1231143 (2013).

13 Chu, V. T. et al. Increasing the efficiency of homology-directed repair for CRISPR-Cas9-induced precise gene editing in mammalian cells. *Nat Biotechnol* 33, 543-548, doi: 10.1038/nbt.3198 (2015).

14 Suenaga, T., Kohyama, M., Hirayasu, K. & Arase, H. Engineering large viral DNA genomes using the CRISPR-Cas9 system. *Microbiol Immunol* 58, 513-522, doi: 10.1111/1348-0421.12180 (2014).

15 Bi, Y. et al. High-efficiency targeted editing of large viral genomes by RNA-guided nucleases. *PLOS Pathog* 10, e1004090, doi: 10.1371/journal.ppat. 1004090 (2014).

16 Mali, P. et al. RNA-guided human genome engineering via Cas9. *Science* 339, 823-826, doi: 10.1126/science.1232033 (2013).

17 Hsu, P. D., Lander, E. S. & Zhang, F. Development and applications of CRISPR-Cas9 for genome engineering. *Cell* 157, 1262-1278, doi: 10.1016/j.cell.2014.05.010 (2014).

18 Rouet, P., Smih, F. & Jasin, M. Introduction of double-strand breaks into the genome of mouse cells by expression of a rare-cutting endonuclease. *Mol Cell Biol* 14, 8096-8106, doi: 10.1128/mcb.14.12.8096 (1994).

19 Rouet, P., Smih, F. & Jasin, M. Expression of a site-specific endonuclease stimulates homologous recombination in mammalian cells. *Proceedings of the National*

*Academy of Sciences of the United States of America* 91, 6064-6068, doi: 10.1073/pnas.91.13.6064 (1994).

20 Jiang, F. et al. Structures of a CRISPR-Cas9 R-loop complex primed for DNA cleavage. *Science* 351, 867-871, doi: 10.1126/science.aad8282 (2016).

21 Jinek, M. et al. Structures of Cas9 endonucleases reveal RNA-mediated conformational activation. *Science* 343, 1247997, doi: 10.1126/science.1247997 (2014).

22 Graham, F. L., Smiley, J., Russell, W. C. & Nairn, R. Characteristics of a human cell line transformed by DNA from human adenovirus type 5. *The Journal of general virology* 36, 59-74, doi: 10.1099/0022-1317-36-1-59 (1977).

23 Fallaux, F. J. et al. Characterization of 911: a new helper cell line for the titration and propagation of early region 1-deleted adenoviral vectors. *Hum Gene Ther* 7, 215-222, doi: 10.1089/hum.1996.7.2-215 (1996).

24 Karakus, U. et al. MHC class II proteins mediate cross-species entry of bat influenza viruses. *Nature* 567, 109-112, doi: 10.1038/s41586-019-0955-3 (2019).

25 Hashimoto-Gotoh, T., Franklin, F. C., Nordheim, A. & Timmis, K. N. Specific-purpose plasmid cloning vectors. I. Low copy number, temperature-sensitive, mobilization-defective pSC101-derived containment vectors. *Gene* 16, 227-235, doi: 10.1016/0378-1119 (81) 90079-2 (1981).

26 Ruzsics, Z. et al. Transposon-assisted cloning and traceless mutagenesis of adenoviruses: Development of a novel vector based on species D. *Journal of virology* 80, 8100-8113, doi: 10.1128/JVI.00687-06 (2006).

27 Senturk, S. et al. Rapid and tunable method to temporally control gene editing based on conditional Cas9 stabilization. *Nature communications* 8, 14370, doi: 10.1038/ncomms14370 (2017).

28 Yuen, K. S., Chan, C. P., Kok, K. H. & Jin, D. Y. Mutagenesis and Genome Engineering of Epstein-Barr Virus in Cultured Human Cells by CRISPR/Cas9. *Methods Mol Biol* 1498, 23-31, doi: 10.1007/978-1-4939-6472-7_2 (2017).

29 Sirena, D., Ruzsics, Z., Schaffner, W., Greber, U. F. & Hemmi, S. The nucleotide sequence and a first generation gene transfer vector of species B human adenovirus serotype 3. *Virology* 343, 283-298, doi: 10.1016/j.virol.2005.08.024 (2005).

30 Riedl, A., Gruber, S. & Ruzsics, Z. Novel conditional plasmids regulated by metabolic switches provide versatile tools for genetic engineering in *E. coli*. *Plasmid in-press* (2020).

31 Datsenko, K. A. & Wanner, B. L. One-step inactivation of chromosomal genes in *Escherichia coli* K-12 using PCR products. *Proceedings of the National Academy of Sciences of the United States of America* 97, 6640-6645, doi: 10.1073/pnas.120163297 (2000).

32 Suzuki, M. et al. Preferable sites and orientations of transgene inserted in the adenovirus vector genome: The E3 site may be unfavorable for transgene position. *Gene therapy* 22, 421-429, doi: 10.1038/gt.2014.124 (2015).

33 Anastassiadis, K. et al. Dre recombinase, like Cre, is a highly efficient site-specific recombinase in *E. coli*, mammalian cells and mice. *Dis Model Mech* 2, 508-515, doi: 10.1242/dmm.003087 (2009).

34 Gibson, D. G. et al. Enzymatic assembly of DNA molecules up to several hundred kilobases. *Nat Methods* 6, 343-345, doi: 10.1038/nmeth. 1318 (2009).

35 Anderson, R. D., Haskell, R. E., Xia, H., Roessler, B. J. & Davidson, B. L. A simple method for the rapid generation of recombinant adenovirus vectors. *Gene therapy* 7, 1034-1038, doi: 10.1038/sj.gt.3301197 (2000).

36 Clackson, T. et al. Redesigning an FKBP-ligand interface to generate chemical dimerizers with novel specificity. *Proceedings of the National Academy of Sciences of the United States of America* 95, 10437-10442, doi: 10.1073/pnas.95.18.10437 (1998).

37 Lee, D. et al. No more helper adenovirus: production of gutless adenovirus (GLAd) free of adenovirus and replication-competent adenovirus (RCA) contaminants. *Exp Mol Med* 51, 127, doi: 10.1038/s12276-019-0334-z (2019).

38 McDade, J. R., Waxmonsky, N. C., Swanson, L. E. & Fan, M. Practical Considerations for Using Pooled Lentiviral CRISPR Libraries. *Curr Protoc Mol Biol* 115, 31 35 31-31 35 13, doi: 10.1002/cpmb.8 (2016).

39 Lee, C. S. et al. Adenovirus-Mediated Gene Delivery: Potential Applications for Gene and Cell-Based Therapies in the New Era of Personalized Medicine. *Genes Dis* 4, 43-63, doi: 10.1016/j.gendis.2017.04.001 (2017).

40 Giese, M. DNA-antiviral vaccines: new developments and approaches—a review. *Virus Genes* 17, 219-232, doi: 10.1023/a: 1008013720032 (1998).

SEQUENCE LISTING

The patent contains a lengthy sequence listing. A copy of the sequence listing is available in electronic form from the USPTO web site (https://seqdata.uspto.gov/docdetail?docId=US12716064B2). An electronic copy of the sequence listing will also be available from the USPTO upon request and payment of the fee set forth in 37 CFR 1.19(b)(3).

The invention claimed is:

1. A circular DNA molecule for rescuing recombinant adenoviruses comprising a recombinant adenoviral genome with two inverted terminal repeats (ITRs) flanking the genome ends, wherein at least one of the ITRs is in close proximity to or partially overlaps a target sequence adjacent to a PAM sequence, wherein the target sequence is configured to guide an RNA-guided DNA endonuclease to generate a DNA double strand break at the external end of or in close proximity outside the external end of the respective ITR.

2. The circular DNA molecule according to claim 1, wherein each of the two ITRs are in close proximity to or partially overlap with a target sequence adjacent to a PAM sequence.

3. The circular DNA molecule according to claim 2, wherein the target sequences that are in close proximity to or partially overlap the two ITRs are identical or different.

4. The circular DNA molecule according to claim 1, wherein the target sequence or the PAM is located adjacent to the external end of the ITR.

5. The circular DNA molecule according to claim 1, wherein the target sequences that are in close proximity to or partially overlap with the two ITRs are identical.

6. The circular DNA molecule according to claim 1, wherein the PAM and/or the target sequence are at least partially overlapping with the external end of the ITR, wherein the target sequence is configured to guide an RNA-guided DNA endonuclease to generate a DNA double strand break at the external end of the respective ITR.

7. The circular DNA molecule according to claim 1, wherein the circular DNA molecule is a bacterial artificial chromosome.

8. The circular DNA molecule according to claim 1, wherein the circular DNA molecule is a high copy plasmid.

9. The circular DNA molecule according to claim 1, additionally comprising an expression cassette,
- wherein said at least one expression cassette is selected from the group consisting of an expression cassette for at least one guide-RNA (gRNA), and an expression cassette for an RNA-guided DNA endonuclease generating DNA double strand breaks, and wherein the said at least one expression cassette is located between the two ITRs outside the adenoviral genome.

10. The circular DNA molecule according to claim 1, wherein the adenoviral genome is a human adenoviral vector genome.

11. The circular DNA molecule according to claim 1, wherein the adenoviral genome is a simian adenoviral vector genome.

12. The circular DNA molecule according to claim 1, wherein the adenoviral genome is an adenoviral vector genome.

13. A kit for rescuing recombinant adenoviruses comprising
- a) a circular DNA molecule according to claim 1, and
- b) an RNA-guided DNA endonuclease or a nucleic acid molecule encoding an RNA-guided DNA endonuclease,
- c) one or more gRNAs or one or more nucleic acid molecules encoding one or more gRNAs for guiding the RNA-guided DNA endonuclease to the targeting sequences of the circular DNA molecule, and/or
- d) cells capable of supporting the replication of recombinant adenoviruses.

14. The kit according to claim 13, wherein the kit comprises cells capable of supporting the replication of recombinant adenoviruses, wherein the cells express an RNA-guided DNA endonuclease.

15. An in vitro method for rescuing recombinant adenoviruses, the method comprising
- a) providing cells capable of supporting the replication of recombinant adenoviruses,
- b) introducing into said cell a circular DNA molecule according to claim 1 comprising a recombinant adenoviral genome with two inverted terminal repeats (ITRs) flanking the genome ends, wherein at least one of the ITRs is in close proximity to or partially overlaps a target sequence adjacent to a PAM sequence, wherein each of the target sequences are configured to guide an RNA-guided DNA endonuclease to generate a DNA double strand break at the external end of or in close proximity outside the external end of the respective ITR,
- c) providing inside the cell an RNA-guided DNA endonuclease by transfection or viral delivery and at least one gRNA for guiding the RNA-guided DNA endonuclease to the target sequence of the circular DNA molecule,
- d) linearizing the recombinant adenoviral genome by the RNA-guided DNA endonuclease-mediated double strand break within the cells, and
- e) collecting viral particles from the cell supernatant.

16. The circular DNA molecule according to claim 1, wherein the adenoviral genome is a first-generation adenoviral vector genome comprising at least one transgene.

17. The kit according to claim 13, wherein the kit comprises cells suited for rescuing recombinant adenoviruses,
wherein the cells are 293 cells or A549 cells and
wherein the cells express SpCas9.

* * * * *